United States Patent [19]

Abele

[11] Patent Number: 4,501,009
[45] Date of Patent: Feb. 19, 1985

[54] APPARATUS FOR STEREOTACTIC SURGERY
[75] Inventor: Manlio Abele, Garden City, N.Y.
[73] Assignee: New York University, New York, N.Y.
[21] Appl. No.: 293,526
[22] Filed: Aug. 17, 1981
[51] Int. Cl.³ .............................................. G03B 41/16
[52] U.S. Cl. ........................................ 378/19; 378/4
[58] Field of Search ...................... 378/19, 20, 11, 12, 378/14

[56] References Cited
U.S. PATENT DOCUMENTS
4,150,297 4/1979 Borggren .............................. 378/20
4,377,867 3/1983 Oliver .

Primary Examiner—Craig E. Church
Attorney, Agent, or Firm—J. David Dainow

[57] ABSTRACT

The invention relates to improvements in an apparatus employing computerized tomography for diagnosis and stereotactic surgery. A new tomographic scanning system is shown including a base, a source of penetrating energy, a detector which produces scanning signals, source and detector positioning means, a C-shaped frame having top and bottom arms, means for securing the detector and source to the top and bottom arms, and first, second, and third drive means for positioning the frame.

17 Claims, 14 Drawing Figures

FIG. 12

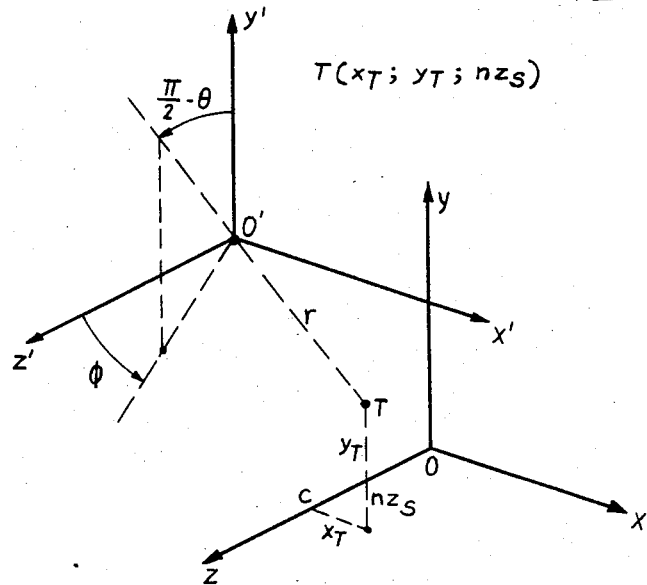

STEREOTACTIC GUIDE $x', y', z'$ — THE FRAME OF REFERENCE OF THE STEREOTACTIC GUIDE SYSTEM, WITH THE ORIGIN O' AT THE CENTER OF ROTATION OF THE PROBE. AXES $x', y', z'$ ARE PARALLEL TO AXES $x, y, z$ RESPECTIVELY.

$x, y, z$ — THE FIXED FRAME OF REFERENCE OF THE SCANNER. THE PLANE $x, y$ IS THE SCANNING PLANE, WITH THE ORIGIN O AT THE CENTER OF ROTATION OF THE SCANNER.

$x$ — HORIZONTAL AXIS POINTING TO THE SURGEON'S RIGHT.

$y$ — VERTICAL AXIS POINTING UP.

$z$ — AXIS PERPENDICULAR TO THE SCANNING PLANE, POINTING TOWARD THE SURGEON.

$r, \theta, \phi$ — THE SPHERICAL FRAME OF REFERENCE, WITH THE ORIGIN AT O'.

$r$ — PENETRATION OF THE PROBE $\theta$ — ANGLE WITH RESPECT TO THE HORIZONTAL PLANE. A POSITIVE VALUE OF $\theta$ CORRESPONDS TO THE PROBE POINTING DOWN.

$\phi$ — ANGLE FORMED BY THE VERTICAL ARC OF THE GUIDE SYSTEM WITH RESPECT TO THE $y', z'$ PLANE. A POSITIVE VALUE OF $\phi$ CORRESPONDS TO AN ANTI-CLOCKWISE ROTATION ABOUT $y'$.

$z_s$ — THE INCREMENTAL STEP OF THE SCANNING PLANE USED IN THE SCANNING SEQUENCE.

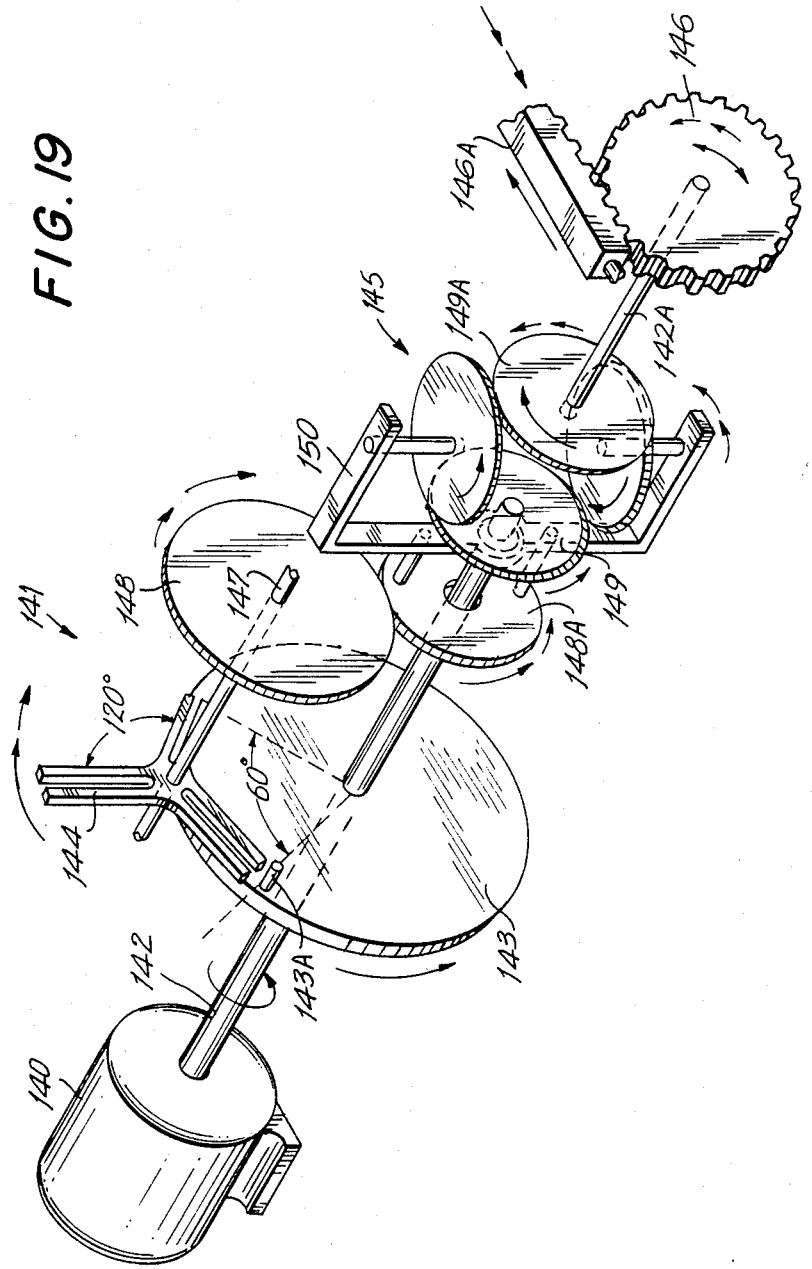

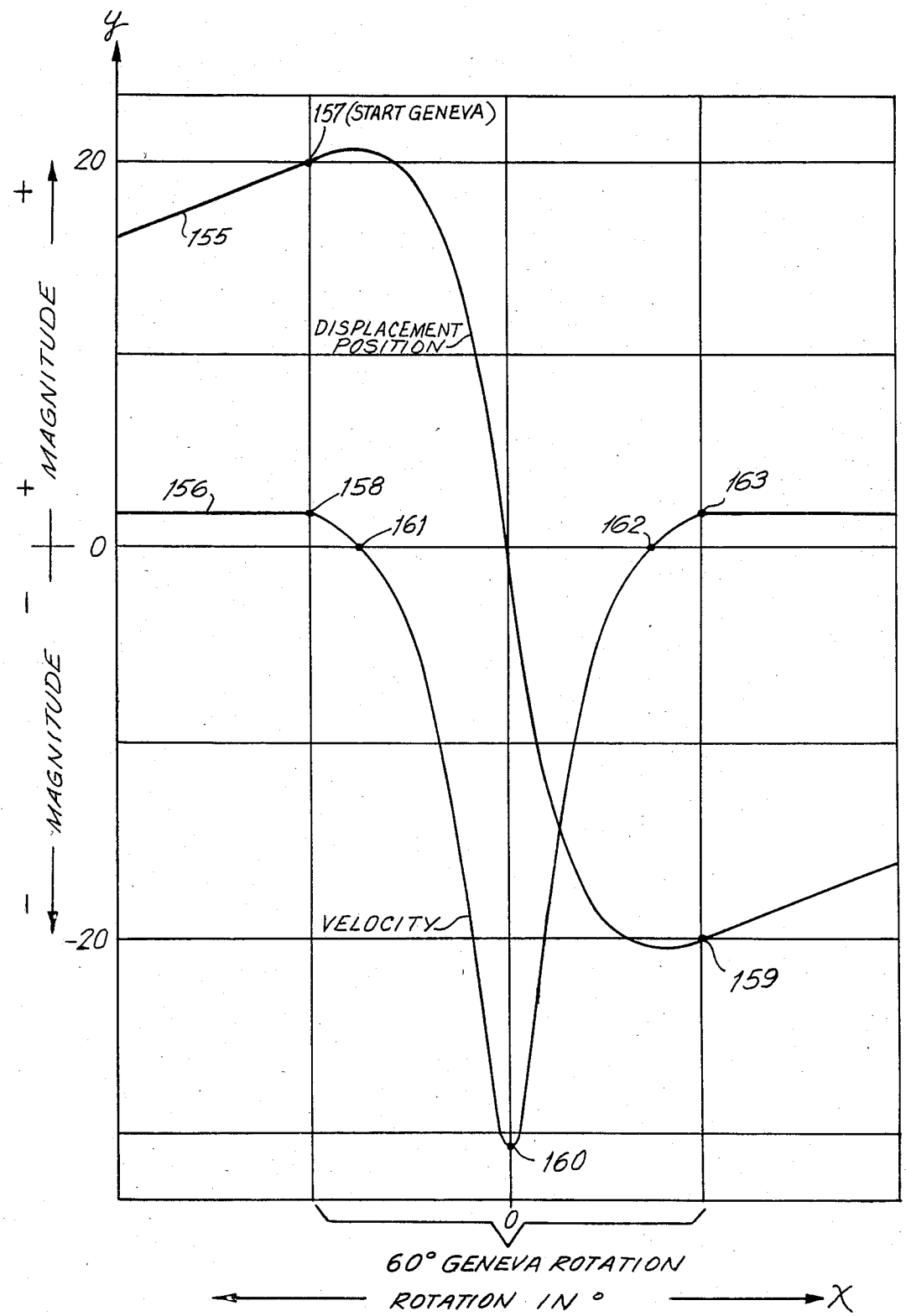

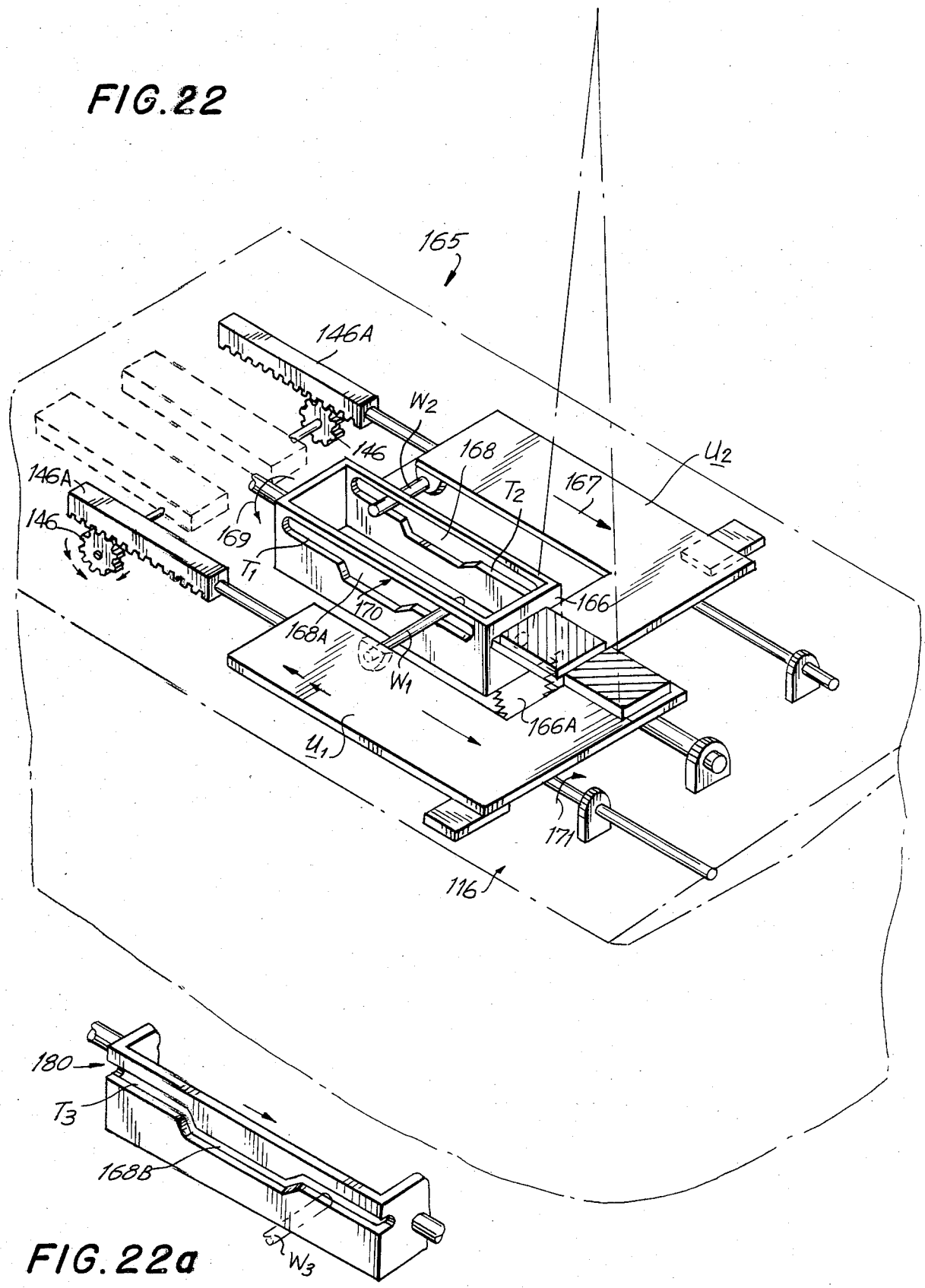

APPARATUS FOR STEREOTACTIC SURGERY

BACKGROUND OF THE INVENTION

This invention relates to a method and apparatus employing computerized tomography for diagnosis and stereotactic surgery. While the invention will be disclosed with particular reference to the requirements of brain surgery, it will be apparent that the invention may advantageously be employed for other procedures.

Stereotactic surgery is a sub-specialty of neurosurgery and defines a class of operations in which probes, such as cannulae, needles, forceps or electrodes are placed into brain regions or anatomical targets that are not visible on the surface of the brain. The general location of these regions is determined by measurements from landmarks visualized by X-ray or other means, such measurements being based on atlases derived from anatomical studies and autopsy. Because of anatomical variability, more precise location in any single patient may be determined by physiological responses in that patient. The degree of success in stereotactic surgery depends upon the experience of the surgeon as well as the precision of the stereotactic instrument and radiologic brain imaging technique.

A stereotactic instrument is a guiding device used in human neurosurgery for the purpose of directing an instrument to a specific point within the brain by radiographic or other visualization of landmarks, through a small opening in the skull. Stereotactic instruments are constructed to afford the surgeon reliably reproducible accuracy in placing instruments into target areas. Proper positioning of the probe is often verified by x-rays to control errors in calculation and to correct deflection of the probe during insertion. Physiologic parameters may be used to further define the optimal target.

At the prresent time, stereotactic instruments are used most frequently, but not exclusively, in the following operations.

Thalamotomy for parkinsonism and other types of tremor,
Electrode implantation for epilepsy,
Needle and/or magnet insertion for aneurysm thrombosis,
Thalamic or subthalamic operations for involuntary movements such as chorea or hemiballismus,
Ablation of deep cerebellar nuclei for spasticity,
Cingulotomy and thalamic or subthalamic surgery for pain,
Mesencephalotomy for pain,
Ablations for subcortical temporal lobe structures for treatment of epilepsy,
Psychosurgical procedures,
Implantation of depth stimulating electrodes for pain,
Insertion of forceps or needle for obtaining biopsy specimens,
Foreign body removal, and
Implantation of radioactive material
Biopsy or treatment of tumors.

The list is presented only to give examples for some applications. It is not required to hit a point in space, but to hit a volume or make a lesion within a mass. The purpose of stereotactic apparatus is to guide the advance of an electrode or other probe accurately and in a controlled fashion to a given point in space, relative to the apparatus, the stereotactic target. Thus, when the apparatus is attached to the skull, the probe can be advanced to a given geographical point within the cranial cavity, near the base of the skull, or in the spinal canal. As generally employed, the ventricles or cavities within the brain or other cerebral landmarks are identified roentgenographically or by other means and, by consulting an atlas or other table, the mean distance and direction between the visualized landmark and a given anatomical target are measured. The probe is then inserted to the stereotactic target, that is, the point in space within the cranial cavity which is calculated from the distance and direction between the visualized landmark and the desired target in relation to the coordinate system of the stereotactic apparatus. It is recognized that there is considerable anatomical variability in brain size and shape so that the target point is identified from the atlas or table is only approximate. Usually, where possible, physiological verification may also be obtained. One must distinguish between the anatomical accuracy, which is inexact because of the variability of brains, and the mechanical accuracy, which is a function of the precision of the stereotactic instrument.

In the utilization of computed tomography for stereotactic surgery some targets may be directly visualized in an image, such as a brain tumor.

As previously stated x-ray images of the brain are currently used in neurosurgery to locate the pertinent landmarks. In principle a series of images in orthogonal planes allows the neurosurgeon to determine landmark coordinates. Unfortunately a landmark may not be readily identifiable because of the poor density resolution of conventional x-ray images and uncertainties about the head orientation.

Computerized tomography provides a new imaging technique which not only has high density resolution capabilities, but also provides a quantitative information about the anatomy. In accordance with the invention, computerized tomography can be integrated in a neurosurgical procedure to provide major improvement in target identification.

Basic concepts of CT scanning and the displays related thereto are described in U.S. Pat. No. 3,778,614, issued Dec. 1, 1973, the disclosure of which is specifically incorporated herein by reference.

A comprehensive analysis of the integration of computerized tomography CT in neurosurgery requires a definition of the differences between surgical requirements and the scanning configuration and data presentation in commercial CT scanners which are designed to satisfy diagnostic requirements.

The basic information obtained from a conventional CT image is the value of local tissue density which is used for diagnosis of tissue anomalies. The spatial density distribution generates the information about the anatomy and the location and dimensions of tissue anomalies. Thus for diagnostic purposes, spatial resolution in the image plane, as well as thickness of the tissue "slice" covered in each scanning, are selected to achieve a maximum sensitivity in tissue density discrimination. This contrasts with the requirements of a surgical procedure, where the anatomy and in particular the outline of body organs is the dominant parameter to determine either target point or landmark location. Scanning parameters and image reconstruction algorithms must then be selected to obtain a maximum precision in target location measurement while tissue density discrimination may become of secondary importance.

In a normal CT scanner procedure for diagnostic purposes a multiplicity of scans may be taken to explore the entire region of the brain as well as to determine the three-dimensional properties of the tissue element under scrutiny. The distance between scanning planes or slices and the thickness and number of slices depend upon the specific information which is sought by the clinician in each particular case. In a surgical procedure the sequence of scans must provide the spatial coordinates of a target point. Thus, in a general case, the element of volume of interest must be explored uniformly with a sequence of scans at intervals selected to maintain a uniform spatial resolution throughout the element of volume.

With respect to the dimensions of the volume to be scanned, for diagnostic purposes a series of total scans of the head are necessary, while in a surgical procedure the scans may be limited to the region of interest, because by the time the patient is brought into the surgical room, the diagnosis has been completed and conventional scan results are available to the surgeon. Dimensions of the order of 5 cm. of the volume to be imaged during the surgical procedure are adequate for the brain. The surgical scanner can then be designed for partial scanning with two important advantages. First, the limited extent of the partial scanning region makes it possible to achieve a high spatial resolution without increasing the total x-ray dose. Second, size and weight of the gantry of a scanner designed for partial scanning in such a small region may be drastically reduced compared to a conventional scanner.

The above considerations refer primarily to the imaging logic and scanning modality. Additional important considerations have to be made regarding surgical instrumentation and procedure as well as patient handling. First of all, the stereotactic guide and the head support must be designed to minimize their interference with the x-ray beam throughout the scanning sequence. The design of the stereotactic guide can easily be arranged to keep the controls and supports outside of the scanning planes. On the other hand conventional head holders are not so easily adapted to this system because of the relatively small degree of freedom in the location of constraining pins which hold the skull in the proper position. If the pin structure must cross the scanning plane, considerable care has to be taken in the selection of materials and in the design of the support to avoid the creation of strong artifacts throughout the image. However, the design of these surgical components is only a part of the total problem of satisfying both surgical and scanning requirements. It is well known that the image reconstruction requires the acquisition of data over a rotation of the x-ray source of at least 180° in the scanning plane. This has resulted in a closed configuration of all commercial scanners with an opening whose dimensions are dictated by the cross section of the human body. The closed configuration and the position of the scanning plane relative to the patient support makes a commercial scanner hardly suitable for stereotactic surgical procedures since it interferes with the surgeon's access to the surgical area. Both size and shape of the scanner gantry are thus an important factor in the design of an integrated surgical system.

In addition, patient handling procedures for diagnostic purposes may not be suitable for surgical applications. In a commercial scanner, with the exception of gantry tilting, it is the patient support that undergoes axial as well as vertical motion to position a given section of the patient body in the scanning plane. In a surgical procedure a preliminary phase involves arrangement of the patient in a position which satisfies both the surgical and scanning requirement. This phase may involve the control of position and orientation of both scanner gantry and patient support. However, once the preliminary phase is over and the patient's head is locked in its support, the ideal situation is to keep the patient immobile and to confine all motions to the instrumentation including the indexing of scanning positions during the scanning sequence.

In accordance with the invention, the image reconstruction algorithm and the orientation of the image planes are selected to optimize primarily the presentation of tissue anatomy rather than tissue characteristics. In addition, the scanning procedure is limited to a partial scanning of the volume of interest with a spatial resolution uniform in the scanning plane as well as perpendicular to the scanning plane. A low scanning speed to optimize image quality must be selected as a trade-off between x-ray dose within the region of partial scanning and total scanning time of the volume of interest. The dimensions of the volume explored in the partial scanning procedure is selected as a trade-off between surgical requirements and amount of data and computational time. Head holder and stereotactic guide are preferably designed to minimize their interference with the scanning procedure throughout the volume of interest. The gantry is designed to minimize obstructions to the surgeon's access to the surgical area and provide maxiam flexibility in patient positioning. Translations and angular orientations required by the scanning procedure are implemented in the scanner gantry rather than in the patient support. In a preferred embodiment of the invention, safety features are built into the scanner for possible emergencies, including the rapid removal of the gantry from the patient support should the need arise.

Additional features are preferably included to monitor the actual surgical procedure. Upon completion of the target identification phase and adjustment of the orientation controls of the stereotactic guide, the probe is driven into the brain region to reach the depth of the target point. The penetration has to be monitored by measuring the coordinates of the probe tip position prior to reaching the target point. Thus the x-ray system of the scanner is used to monitor the probe tip position at prescribed points of the probe trajectory.

In conjunction with certain of the above-noted objectives, the present invention includes a preferred gantry structure having a generally open configuration which provides better access to the patient and reduced interference by the gantry and associated components with the scanning beam. The approach herein is a basically open C-shape support in contrast to the traditional closed circular support. Two arms of the C-shape define an arc nominally 180° but actually somewhat greater for reasons of practicality.

The basic scanning procedure is to scan across one plane at a time through the specimen by directing the X-ray beam through a succession of parallel or angled orientations all within the particular scan plane, and then to move the scan plane sequentially at 1.5 mm or other selected increments along an axial coordinate perpendicular to these planes. Traditionally the scan is achieved by moving the source in a straight line above the specimen with a similar parallel movement of a detector below the specimen, or by moving the source circumferentially around the specimen with an identical movement of the detector, such that the source and detector remain diametrically opposed with a constant distance between them as the scan occurs. In circular scan procedures the traditional prior art support structure is a closed circular frame around which the source and detector move, thus requiring the patient to be moved axially into the circular frame. The source is caused to move along a circular path with the radiation beam directed radially inward across the center of the circle to a detector at the opposite side of the circumference, and the detector is simultaneously caused to move in the opposite direction. Various arrangements have been used so that after each plane is scanned, the source and detector are circumferentially or laterally returned to their starting position and are axially moved to a next adjacent plane to be scanned.

In the present invention detection is achieved with a new structural arrangement which provides better continuity of detection by scanning during forward movement of the detectors and while the detectors move backwards to return to their starting position, and by using a pair of detectors operated one behind the other in the direction of motion.

The lead detector moves to the rear of the other after each of many incremental movements along the circumferential path, while the source moves essentially continuously through the entire circumferential cycle. The pair of detector units still constitutes a single detector means remaining angularly displaced 180° from the source, but also angularly moveable the same manner as the source. Later the process is repeated in the opposite direction so that there is no need to recycle or reposition the detector when the source begins its reverse circular motion about the frame. The preferred arrangement devised is to have a first detector near the end of its operative cycle followed closely by a second detector which moves into the position and role of the first so that the first can be repositioned behind the second when the second nears the end of its operative cycle.

In order that the invention will be more clearly understood, it will now be disclosed in greater detail with reference to the accompanying drawings, wherein:

FIG. 10A shows part of an alternative tilt frame.

FIGS. 11a–23d are schematic drawings representing the oscillatory motion of the detectors corresponding to FIG. 10.

FIG. 12 is a chart representing angular displacement of the detectors at the opposite extremes of their excursion.

FIG. 13 is a fragmentary perspective view of a patient's skull showing points of rigid engagement.

FIG. 14 is a schematic drawing showing a skull and aperture.

Figure 2:
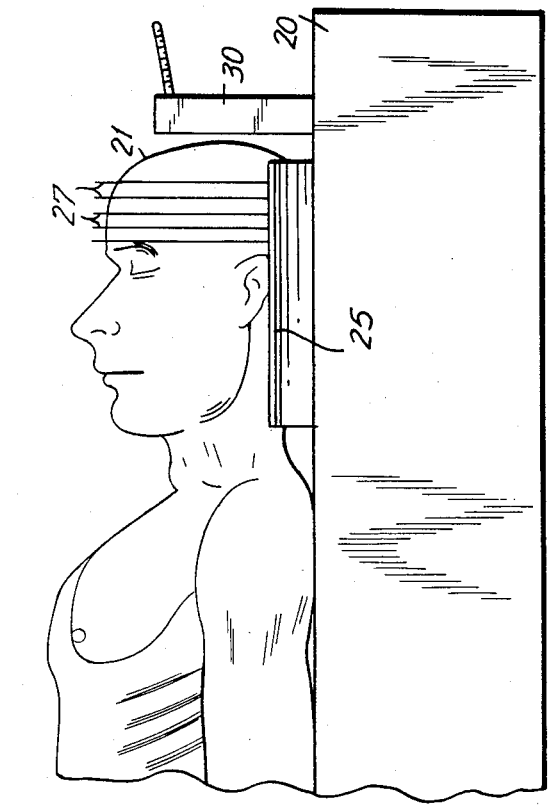
FIG. 2 is a side elevation view of the apparatus of FIG. 1.

The preferred embodiment 110 of the new tomographic scanning system is shown generally in FIG. 1 as a support housing or gantry 111 carrying a radiation source 112 and radiation detection means 113 with various drive means which will be described in greater detail in subsequent paragraphs. Secured to and rotated by the gantry is a generally C-shaped frame 114 having a top arm 115 which carries the radiation source 112, and a bottom arm 116 which carries the detector means 113. Frame 114 is rotatable about center point 117, thereby defining circle 118 which is the path of movement of the source and detector means. The radiation beam 119 is projected along a diameter 120 of the circle, and rotation of frame 114 provides radiation scanning through the center of the circle from all points along the circumference of the circle.

A first drive mechanism 121 provided to rotate the C-frame 114 consists essentially of upper and lower links 122, 123, each having a near end pivotally secured to the gantry and a remote end pivotally secured to the C-frame. More specifically, the near end of typical link 122 is coupled to the gantry by a pair of arms 124, 125 which pivot about fixed points P1, P2 respectively, thus describing circles C1 and C2 respectively. These arms are pivotally secured to the near end of link 122 at pivot points P3, P4 respectively which results in a parallelogram device with link 122 movable between its solid-line position shown, its dotted-line position 122' shown slightly to the right, and a multiplicity of additional positions. Note that pivot point P5 moves to point P5' when the link is moved to position 122', and in so moving P5 will define a circular path C3 the same as C1 and C2.

Link 123 is coupled similarly as link 122 to frame 114, so that movement of link 122 to the right as shown will include equivalent movement of link 123 to the left and rotation of frame 114 and corresponding rotation of frame 114 and corresponding rotation of the radiation beam. For link 123 arm 126 corresponds to upper arm 124; arm 127 corresponds to upper arm 125 but could be a rigid extension of 125 since they have a common pivot point P2, which like points P1 and P6, is fixed on the gantry.

The next subassembly to be considered in more detail is the radiation detector means which in FIGS. 4a–d comprises a pair of essentially identical detector elements designated generally U1 and U2. Further in this figure the radiation source S is indicated by points designated S1, S2, etc. representing successive angular displacements of this source. In the system illustrated in FIG. 4a, the source at S1 provides a beam of X-radiation diverging 8° which strikes an arc a1, on the opposite circumference. Relative to the circle's center 130, arc a1, reprresents 16° of circumference. Typical detector element U1 has an arc length of 24°, and the other element U2 is positioned immediately adjacent U1. Obviously the specimen to be examined is situated generally at the center 130 around which the source rotates.

For the actual scan the beam 131 which penetrates the specimen and strikes the detector at the circumference opposite the detector, rotates at a predetermined and constant angular velocity, indicated for this part of the description to be in a counter-clockwise direction. In order to provide detection means during the entire approximately 180° angular excursion of the source, but also to leave the C-shaped frame essentially open, the detector means comprises a pair of small elements which are moved so that at least one is always aligned with the radiation beam. During the scan, as one detector is fully traversed, the other moves into the position of the first before the first moves out of range so that no hiatus is experienced.

Figure 1:
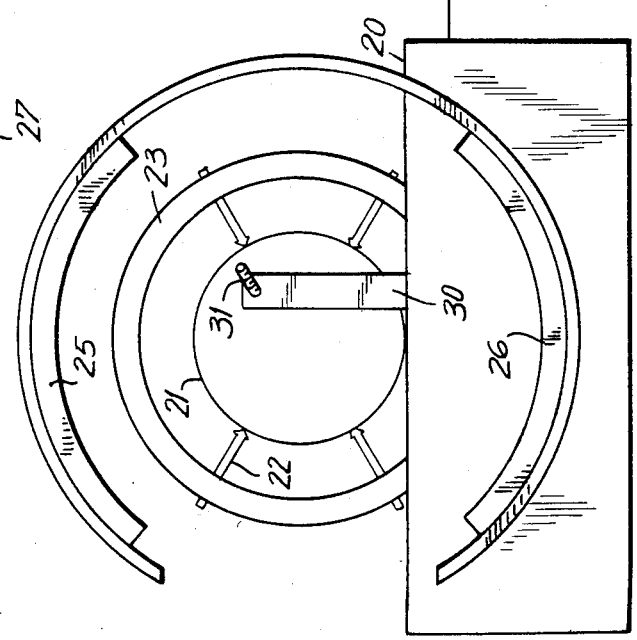
FIG. 1 is end elevation view in schematic representation of a gantry of the new tomographic scanning system showing a radiation source and detectors.
Figure 3:
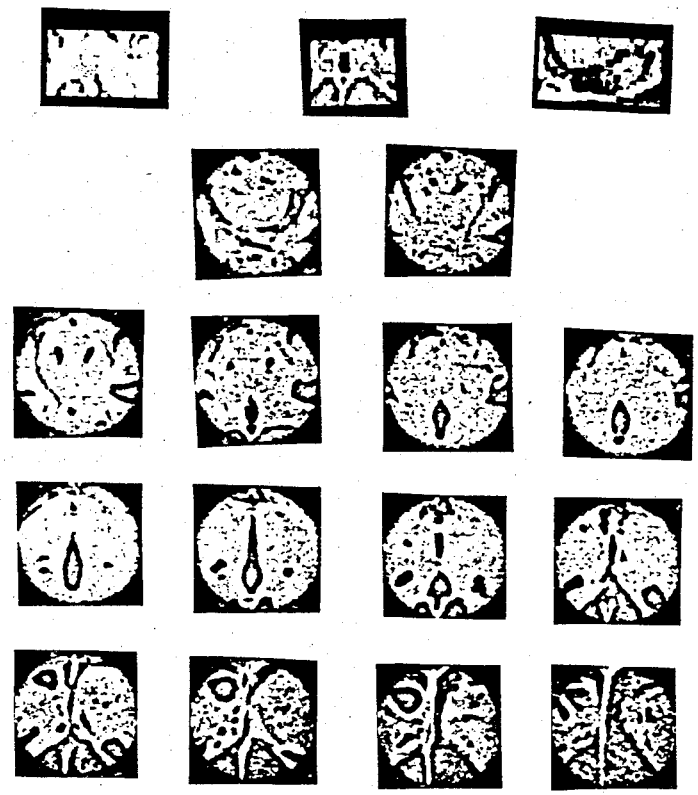
FIG. 3 is a fragmentary schematic view corresponding to FIG. 1, showing parts of the gantry in displaced position.

To achieve the above-described scanning procedure, there is provided the detector means, i.e. the pair of detectors U1 and U2 as a unit having identical displacement and angular velocity as the source, as previously shown by FIGS. 1-3, but these detectors have an additional movement pattern that is semi-independent of the gross rotation already described. More particularly, a typical detector unit, U1 when "actually scanning" moves in an angular direction shown by arrow 132 opposite that of the source shown by arrow 133.

FIGS. 4a-4d illustrate the sequence of movements of the scanning components; however, it should be understood that the source actually moves continuously and element U1 actually moves a short distance in the direction of arrow 132, after which U1 moves out of the way to allow U2 to continue the detection operation without interruption, and U1 is moved to occupy a new position rearward of U2, to be ready to continue the detection when the beam has fully traversed U2. As illustrated, U1 has arcuate length 8° greater than the 16° arc $a_1$, struck by the beam. When the source and the detector means have each moved 8° in the opposite direction at the same time, their relative displacement is 16°, so that the lead edge 134 of U1 will have been scanned by the entire 16° of beam, and 8° of U1's detection surface remains. By FIG. 4c the scan continues with the source having moved 8° further, U1 having moved 16° relative to S, so that U1's trailing edge 135 is still being scanned while U2's lead edge 136 has substantially entered the scan field and thus prevented interruption. Now, between FIGS. 4c and 4d there are 16° of additional scan with the beam impinging on U2 before U1 must again be brought into position, to avoid interruption; during this period U1 is maneuvered in the direction opposite of arrow 132 and U2, to a position behind U2 shown in dotted lines and marked U3 in FIG. 1d.

The mechanism to provide the specific motions of U1 and U2 will be described later, but first note FIG. 5 which illustrates schematically the relative positions and angular displacements of U1 and U2 for an approximately 180° excursion of the C-frame carrying the source and pair of detectors. The two parallel lines extending lengthwise represent the 16° arc struck by the x-radiation beam on the circumferential area to be covered by one detector or the other or parts of both all the time. The column of numbers on the right indicates the degrees of displacement of the beam. Accordingly, at 0° beam displacement detector U1 (24° of arc length) is poised to move. Each horizontal step downward in this chart corresponds to 4° of beam displacement. At 8° of beam angular displacement plus 8° of detector displacement, providing 16° of relative displacement between the beam and U1, the lead edge of U1 will fully traverse the 16° of beam arc as shown adjacent the 8° reference on the right column; at 16° on the right, the rear edge of U1 and the lead edge of U2 are both midway in the beam's arc. Between 20° and 24° U2 provides the full detection, while U1 is returned to a position U1' behind U2, and ready to begin its scanning excursion anew. The sequence of forward and rearward oscillations continues until the C-frame has rotated through 188° as indicated, during which time U1 has experienced 8 trips forward and 7 trips rearward.

Figure 6:
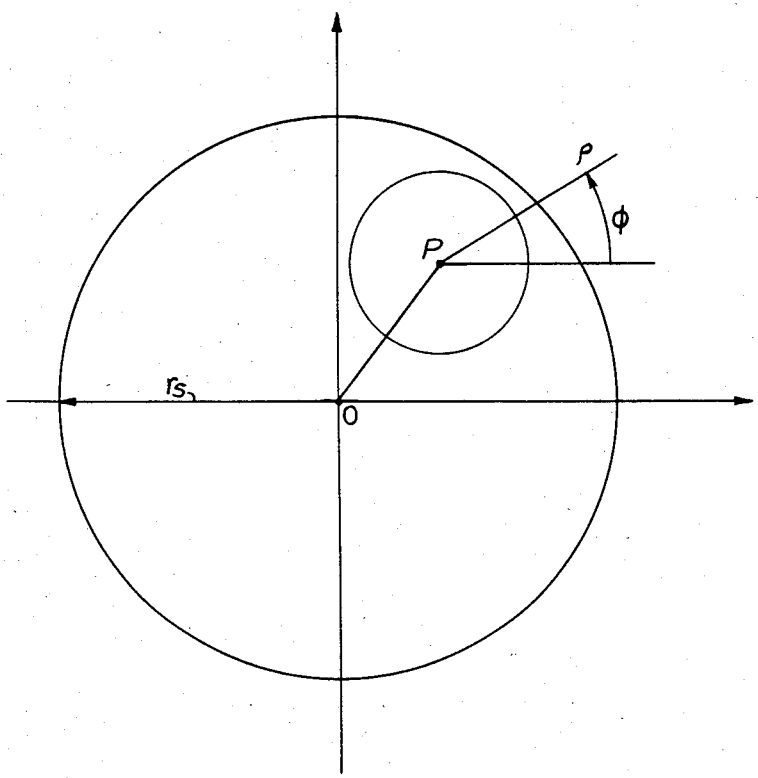
FIG. 6 is an end elevation is schematic representation of the pair of detectors.

In the scanning configuration described herein, the x-ray detectors U1, U2 are each packaged in modules of eight detectors, and the modules include eight pre-amplifier channels. The dimensional relationships of the modules are shown in FIG. 6, where the line marked SP indicates the position of the scanning plane relative to the crystals of the detectors. In this arrangement the boxes containing the pre-amplifiers do not intercept the scanning plane.

The detector modules are assembled in the two units U1, U2 in such a way that the upper surface of the crystals exposed to the x-ray beam is tangent to a circle of 15.56 inches radius. When both units U1, U2 collect data, they move across the x-ray beam on a circular trajectory as indicated in FIGS. 1-3. The two units are built in such a way that the angular interval (measured from the center of scanning) between detectors across the gap between U1 and U2 is equal to the same $\frac{1}{2}°$ interval between two adjacent detectors of each unit.

At each instant of time, 48 detectors are found within the X-ray beam. However, each unit must contain a large number of detectors to maintain the continuity of data acquisition during the intervals of time necessary to move a unit back to its initial scanning position. The scanning module, which houses the x-ray source and detectors rotates with an annular velocity $\omega_o$. In the frame of reference of the scanning module, during the data acquisition phase, the detectors rotate with an angular velocity equal to $2\omega_o$. Assume that at the end of each data acquisition phase, a detector unit is moved back to its initial scanning position with an average angular velocity $\overline{\omega}_r$, where $\overline{\omega}_r$ equals 10. Then the minimum number of detectors $n_o$ in each unit U1, U2 is:

$$\frac{n_o}{n_s} = \frac{\omega_r - 2\omega_o}{\omega_r - 2\omega_o}$$

wherein $n_s$ is the number of detectors within the x-ray beam. $n_s$ is equal to 48; consequently $n_o = 72$ and each unit U1, U2 contains nine detector modules. Each of the two units U1, U2 occupies an arc of 24° over the circle of rotation of source and detectors.

Figure 5:
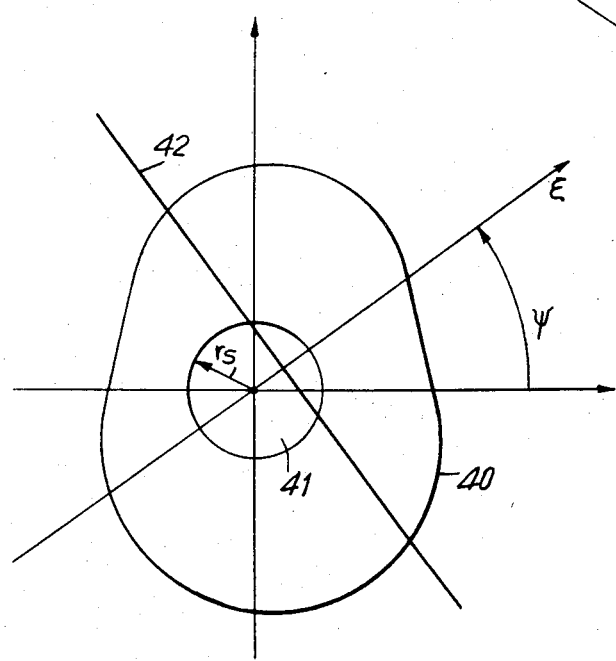
FIG. 5 is a chart showing angular displacement corresponding to FIG. 4.

The schematic of FIG. 5 shows the sequence of positions of both units U1, U2 relative to the X-ray beam during a complete scan. The numbers on the right-hand side correspond to the angular position of the scanning module, and the numbers on the left-hand side correspond to the completion of the traverses of the scan. The data acquisition starts as unit U1 enters the X-ray beam, and it is completed as the same unit leaves the beam at the end of the 180° rotation of the scanning module. The angular oscillation of each detector unit across the X-ray beam covers a 40° arc.

Figure 7:
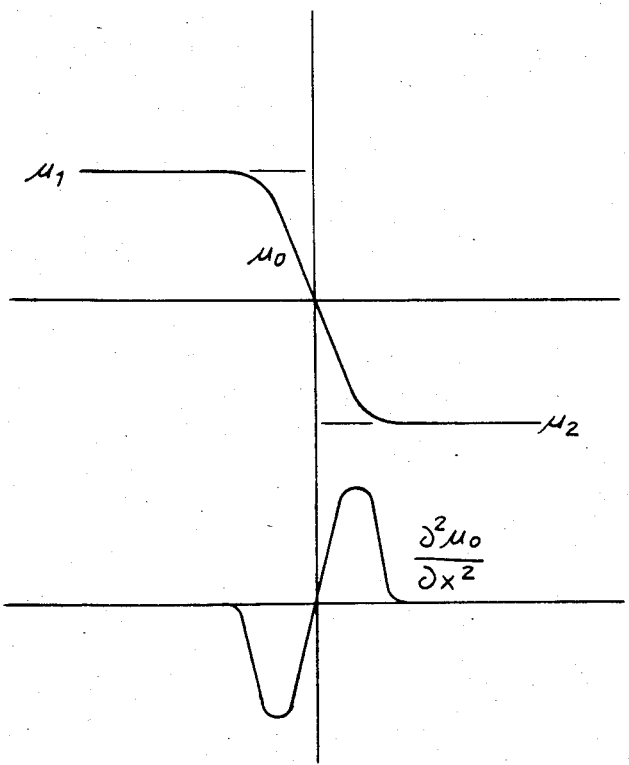
FIG. 7 is a perspective view in schematic representation showing the drive system for moving the detectors.

The mechanical system, which drives the two detector units U1, U2 during the full scan and is shown in FIG. 7, must satisfy the following conditions:
The forward motion, corresponding to the data acquisition phase, is driven at constant angular velocity $2\omega_o$
Before each unit is moved back, it must clear the path for the other unit.
The transition between forward motion and backward high-speed motion must occur with minimum acceleration and jerk.
The system must be reversible, in such a way that at the end of the scan, the next scan is accomplished while the scanning module rotates from 188° back to 0°.

Obviously the kinematics of the detector system must be synchronized with the rotation of the scanning module, which is driven at constant angular velocity $\omega_o$ by a motor housed in the main frame of the scanner. The synchronization is easily achieved by driving the detector system with a stepping motor housed in the rotating scanning module and by controlling the rotation of the stepping motor with the output of an encoder which monitors the angular position of the scanning module.

Figure 4:
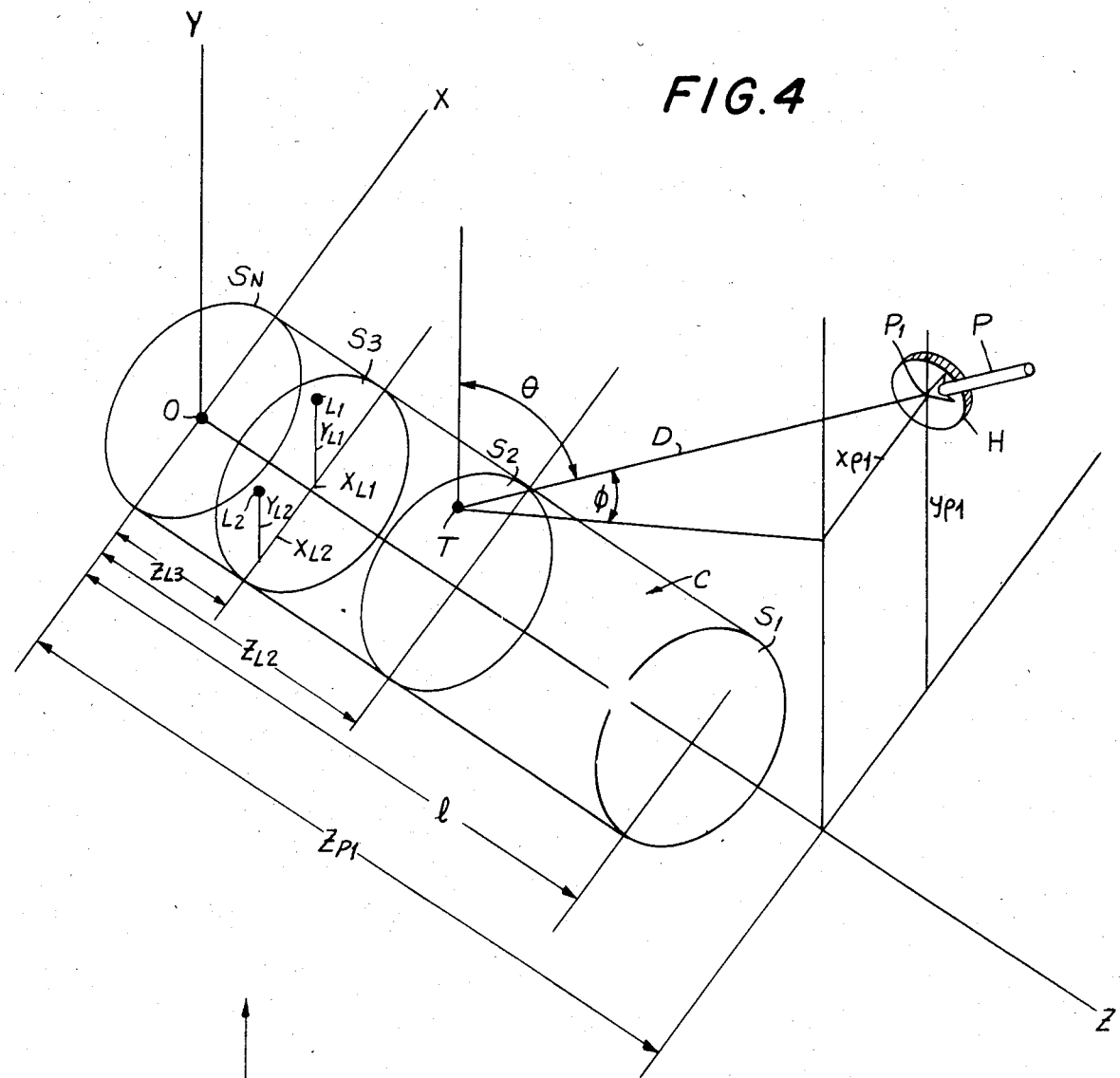
FIG. 4a–4d are schematic drawings showing relative angular displacement of the radiation source and pair of detectors.

Assume that the driver of each detector unit U1, U2 rotates at uniform angular velocity, and that one complete rotation of the driver corresponds to a complete cycle of each unit. Then, in order to implement the kinematics of FIG. 5, the 40° rotation of each detector unit in the scanning module requires a 300° rotation of the driver. The backward motion of each detector unit must occur during the remaining 60° rotation of the driver, while the other detector unit advances by 8° in its forward motion, as indicated in the schematic of FIGS. 4-5, the same driver controls the two units at 180° phase difference, corresponding to a 24° angular interval between U1 and U2, while both units are acquiring data.

In this apparatus the return velocity of each detector will be five times that of its forward velocity of same. Since it was established that the relative forward velocity is $2\omega_o$, five times ($2\omega_o$) equals $10\omega_o$, and will be 1/5 the forward motion time.

The overall positioning mechanism provides two different but interconnected motion controls. One is to move one detector backward to the rear of the other at the appropriate time; and the second is for moving one detector into or out of the path of the beam for active detection while the other is moved in the opposite manner. Each detector package is rigidly attached to a preamplifier to prevent any interference or vibration effect on the detector.

FIG. 7 shows schematically a basic drive mechanism for the new apparatus. A stepping motor 140 is the power unit to rotate each of the detectors into or out of the detection path. This motor has to move each detector forward 40°, and then move that same detector backward in one-fifth the time, so the full cycle of the mechanism must correspond to 48°. It is contemplated that the motor operates continuously.

Figure 8:
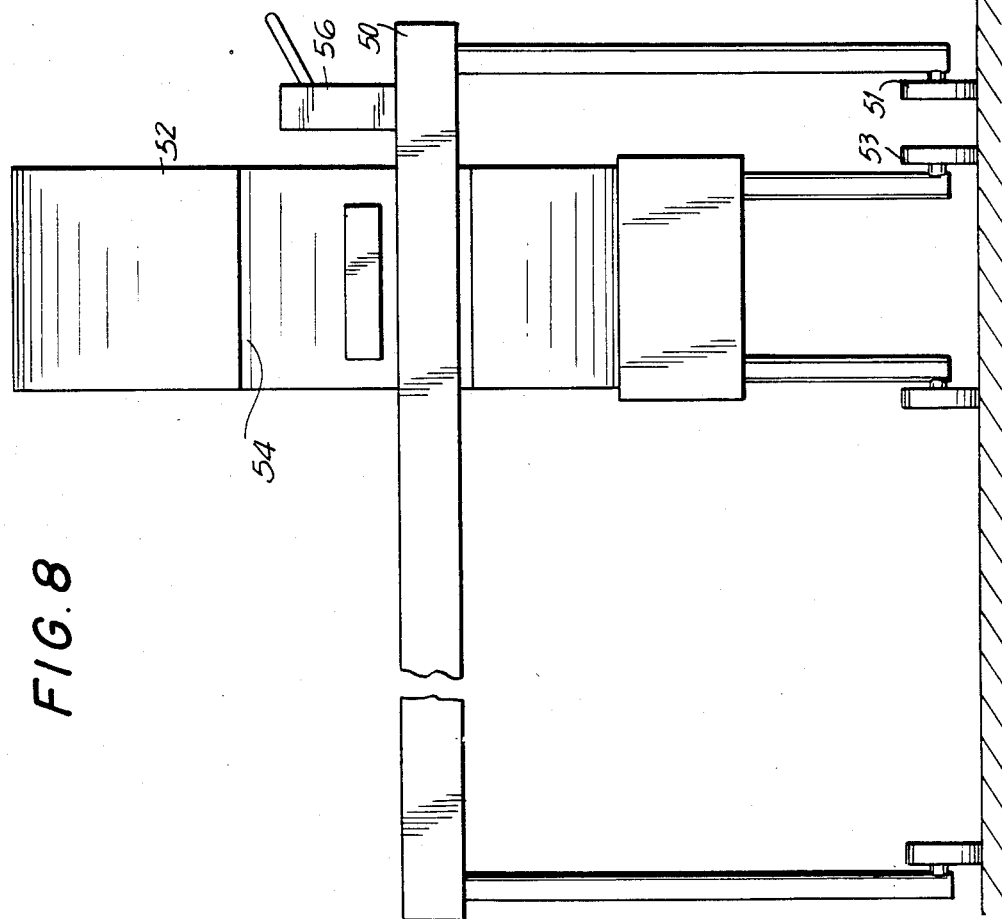
FIG. 8 is a schematic chart further illustrating angular displacement of the detectors.

In order to have continuous detection at all times, including while one detector is moving rearward, 8° over-travel is added to the previously mentioned 40° for a total of 48° on the arc. The technique and mechanism for moving the detectors in their proper sequence is a Geneva mechanism 141 in combination with a reversing transmission 145 as will be described below with further reference to FIG. 8, which shows schematically one full cycle of movement of 48° of one detector. As indicated earlier, the arc length of a detector is 24°. The 40° arc indicates the basic travel path plus 8° more at each end of the over-travel for each detector at each end regardless of direction, so that each lead detector continues to detect while the follower detector first moves rearward and then arrives at its active position.

Figure 10:
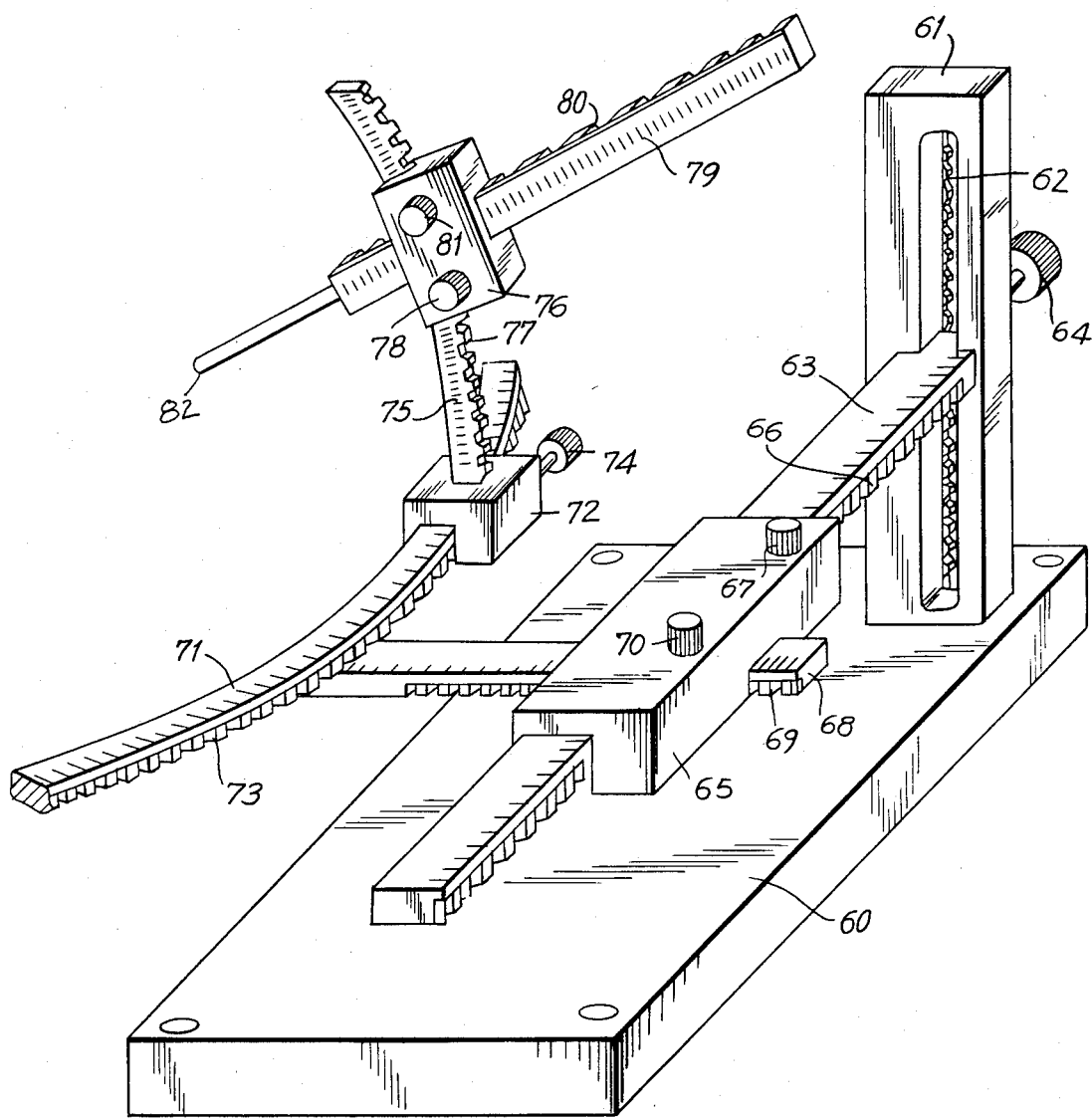
FIG. 10 is a perspective view in schematic representation of the pair of detectors and part of the mechanism for oscillating said detectors.

In FIG. 7 the power source is a stepping motor 140 which drives shaft 142 at a constant angular velocity. This shaft drives wheel 143 of the Geneva mechanism 141 and gear 149 of the differential 145 at the same constant velocity. Normally the output gear 149A of the differential and connected detector drive gear 146 will rotate at the same velocity and in the opposite direction as differential gear 149. FIG. 10 shows gear 146 and rack 146A driving each detector axially in the direction of arrow 167 in the normally forward direction prior to reversal of each detector to a position behind the other detector.

The Geneva element 144 is rotated 120° by pin 143A during 60° of rotation of wheel 143, the Geneva element 144 rotating oppositely of gear 143. Shaft 147, driven by the Geneva element, drives gear 148 similarly as the Geneva element, also in a direction opposite wheel 143 and shaft 142. In FIG. 7 single curved arrows indicate the forward direction of elements and of the detectors; double arrows, one behind another, indicate the rearward direction as effectuated by the Geneva element 144 mechanism. The ratio of velocities of wheel 143 to element 144 is 2:1 by virtue of the 120°:60° respective rotations of these components. Gear 148 and mating gear 148A produce a velocity change, such that gear 148A rotates six times as fast and in the opposite direction as gear 149. Gear 148A is coupled to and causes frame 150 to rotate in the opposite direction as gear 149, which superimposes the velocity of 148A onto 149 so that the differential output gear 149A rotates backward five times faster than it rotated forward; this reversal occurs only during the 60° rotation of wheel 143 when the Geneva element 144 is engaged.

Figure 9:
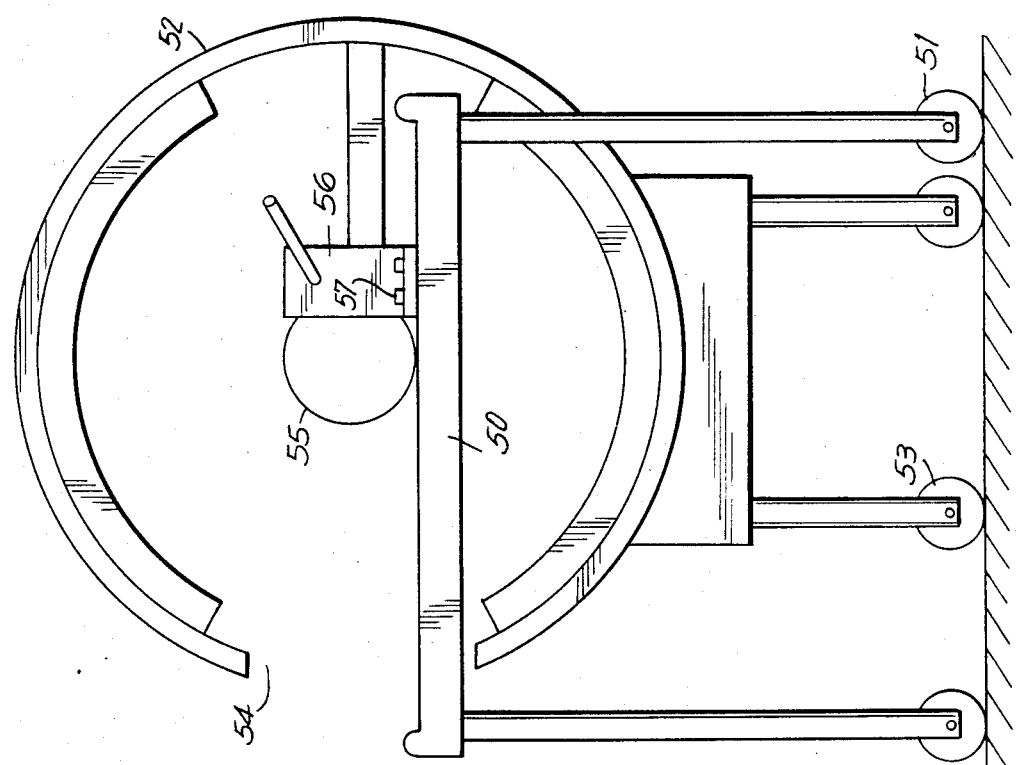
FIG. 9 is a chart showing a plot of displacement and velocity of a detector before, during and after its reverse movement.

Angular position and angular velocity of gear 146 are plotted in FIG. 9 versus the angular position of input gear 149. One observes that there is no discontinuity in the angular velocity at the positions where the driver of the Geneva mechanism engages and disengages the three-prong element 144. As a result, the forward rotation of gear 146 continues for approximately an additional 7.5° angular rotation of gear 149, and the opposite happens at the end of the backward motion phase. This smooth transition between forward and backward rotations greatly simplifies the problem of withdrawing a detector unit from the scanning path at the end of each scanning plane in order to clear the path for the other unit.

The 8° travel of a detector in returning relative to the total 48° is one-sixth; the Geneva mechanism 141 of FIG. 7 has a 120° rotation relative to the 60° rotation of the driver of a complete circle to provide the proper motion. From the stepping motor 140, one full revolution of the output shaft 142 represents 360° on element 143 of the Geneva mechanism 141. This 360° of wheel 143 corresponds to the 48° arc of movement for the full cycle of the detector. Therefore the return trip has to occur within 60°, which is indicated as one segment of the Geneva gear 144.

Refer now to FIG. 9 as it relates to FIG. 7. FIG. 9 is a graph where the horizontal coordinate or abscissa X represents degrees of rotation of the drive mechanism; the vertical coordinate, or ordinate Y represents magnitude of the upper curve 155 which corresponds to displacement or position of one detector package, and the lower curve 156 which corresponds to velocity of that package, whereever it is on its movement path. Accordingly, point 157 on the graph is the beginning of engagement of the Geneva mechanism. Prior to point 158 on the velocity curve the detector had been moving forward constantly; at point 158 velocity in the rearward direction begins to increase. Point 159 on the position curve 155 indicates that the detector has moved through 60° on the Geneva mechanism and is ready to start moving forward again. The curve from point 158 to 160 indicates that the velocity which was forward but slow, i.e., slightly greater than zero, has gone to zero velocity at point 161 and then has accelerated in the rearward direction to a maximum at point 160 and then slows down until it gets to point 162, where it is again zero and then begins a slight acceleration to point 163, where it has started its normal forward motion at a constant velocity again. This is the velocity pattern that is caused by the Geneva mechanism, i.e., it engages and starts slowly and then has a very high acceleration or, in this case, negative acceleration and then slows down to its original position.

According to this preferred embodiment the method for removing each detector unit from the path of the other is indicated schematically in FIG. 6 and in structural detail in FIG. 10. At the end of the each scanning phase, until U1 or U2 is tilted about its pivot axis by an angle large enough to remove the solid state detector hands from the path of the other unit. At the end of the backward motion phase the unit is tilted back to its scanning position. Because of the radial arrangement of the detector modules, by tilting the units away from the center of scanning, one minimizes the interference between the units during the engagement and disengagement phases. To provide a fail-safe system wherein one detector cannot crash into the other while moving rearward to prepare for recycling forward, an intermediate pivoting frame is provided whereby tilting motion of one detector automatically controls the other detector and its position relative to the first. As indicated earlier the gross forward and rearward axial motion of each detector is provided by the drive system illustrated in FIG. 7 with gear or pinion 146 and its associated rack 146A as the output drive component.

Figure 11:
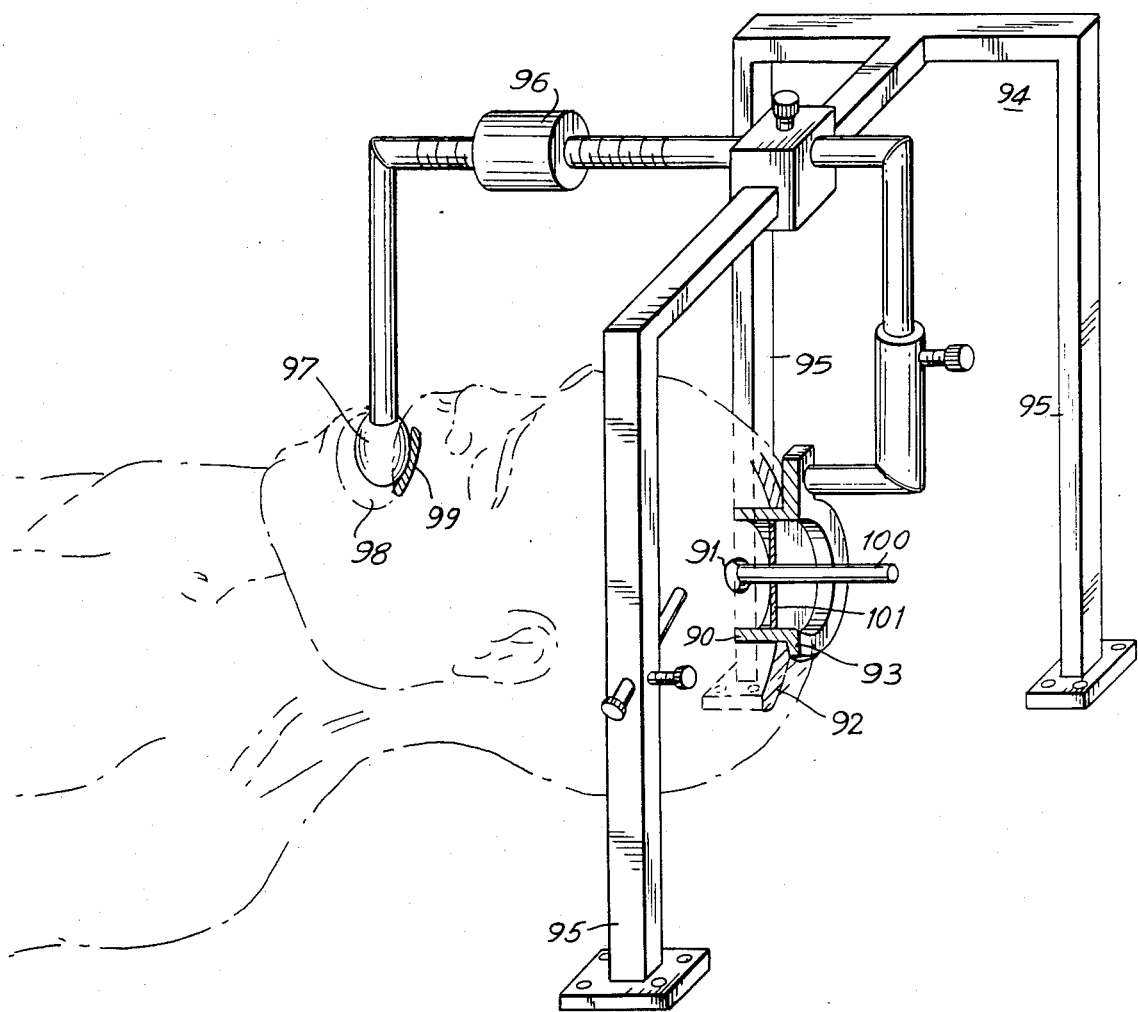

FIG. 10 illustrates schematically the lower arm 116, and detector means 113 corresponding to the same components shown in FIG. 1; FIG. 10 also includes the drive means mechanism 146, 146A as shown earlier in FIG. 7. The drive means as shown automatically provides the correct axial motion to each detector element; the tilt means mechanism 165 is shown in FIG. 10 and its overall sequence of operations is indicated in FIG. 11 as described below.

The diagram FIGS. 11A-D show an entire cycle of the pair of detector units U1 and U2. In 11A the four-sided figure 166 corresponds to the frame 166 in FIG. 10 which is situated to engage both detector units and assure that each will tip or pivot at the appropriate time and therefore not strike the other upon its return stroke. Each detector unit has a guide wheel or cam follow pint, designated W1 and W2 respectively. Each follower is operative in a cam or guide groove indicated as T1 and T2 respectively in FIG. 11, with the same designations in frame 166 in FIG. 10. It should further be noted that the relative positions of the detector units and their follower pins W1 and W2 in FIG. 10 correspond closely with the positions indicated schematically in FIG. 11A.

As indicated in FIG. 10 when detector U2 moves forward in the direction of arrow 167, its pin or wheel W2 will approach the depressed area 168 which has a length of 8° with respect to the scan movement of the x-ray beam. The entire movement of each detector is 40°, such that the 8° area represents 1/5 of the total. When pin W2 reaches area 168, the greater depth of the slot allows frame 166 to tip in a counter-clockwise direction indicated by arrow 169 with the result that the guide surface 170 on the opposite side of frame 166 engages and drives follower pin W1 of detector U1 downward, thereby pivoting detector U1 clockwise as indicated by arrow 171.

Figure 23A:
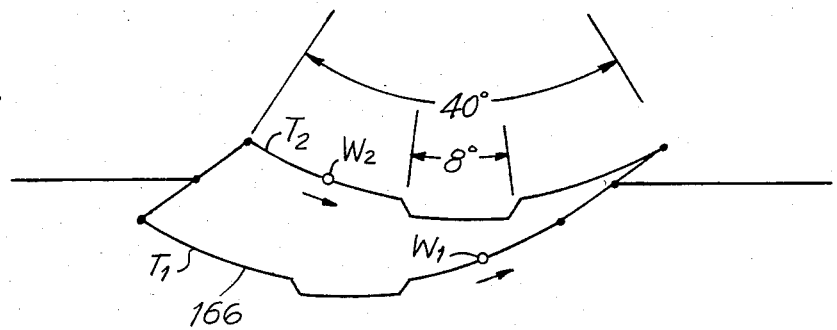
Figure 23B:
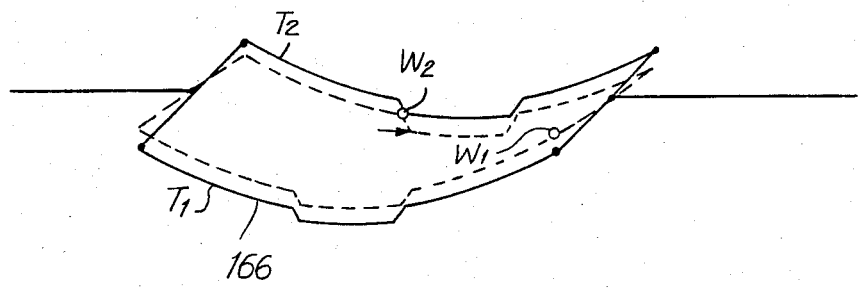
Figure 23C:
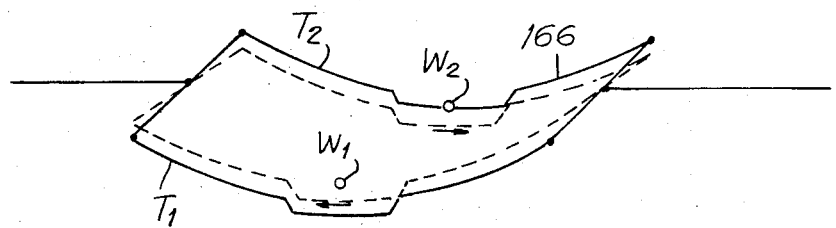
Figure 23D:
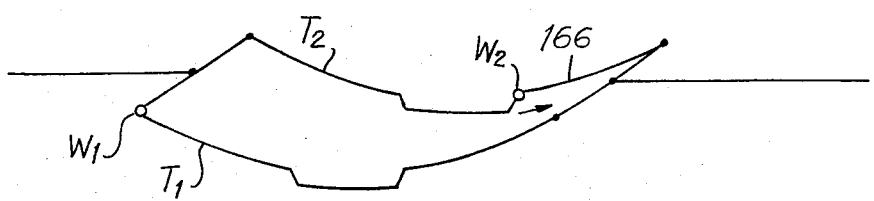

Returning now to FIG. 23a and 23b, it can be seen that pin or wheel W2 is approaching the depression while detector U1 as indicated by its pin W1 is moving in the same direction and is farther ahead. In other words, U1 is leading U2 and both are situated to be operative in tandem as X-ray detectors. FIG. 11b illustrates that as U1 reaches the end of its excursion, U2 has arrived at the depression which will cause tilting. Accordingly, the frame 166 quickly tilts slightly before the detector U1 starts its return travel. Since the return trip takes place about five times faster than the forward motion, and since the tilt depression area is about 1/5 of the total length of travel indicated, the U1 detector will return the full distance during the time that the U2 detector is associated with the recess area. Accordingly the U1 detector will be tilted so as to avoid striking the U2 detector during the entire return trip of the U1 detector. FIG. 11c illustrates a moment in time when the U2 detector has traversed half of the tilt zone while the U1 detector has traversed half of the entire scanning area which, as stated before, is five times the arcuate length of the tilt zone. Finally, in FIG. 11d, the U1 detector has returned to its starting point and the U2 detector has completed its travel in the tilt zone so that the tilt frame 166 returns to its normal position, and the U1 detector ceases being tilted. Now, the U1 detector can begin to travel forward again and follow along behind the U2 detector with both of these members being upright and untilted and with no danger of one striking the other since they are traveling in the same direction at the same speed, one behind the other.

In FIG. 10 there are spring means which urge frame 116 to tilt whenever pin W2 is in cam area 168 or pin W1 is in cam area 168A. While W2 is in zone 168 the frame remains tilted, so that guide surface 170 forces pin W1 and detector U1 to be tilted during its entire reverse motion so that collision with U2 is prevented. Cam track T3 in FIG. 10A is a variation of track T1 in FIG. 10. In T3 cam portion 168B positively engages a pin W3 so that springs are not required and there is no risk of a detector not being tilted out of the way on its return move. In FIG. 10A pin W3, after being tilted, slides out of track T3 and travels rearward in a tilted condition until it re-enters track T3 at 180. With regard to FIG. 10A, parts not shown correspond to those in FIG. 10.

Figure 13:
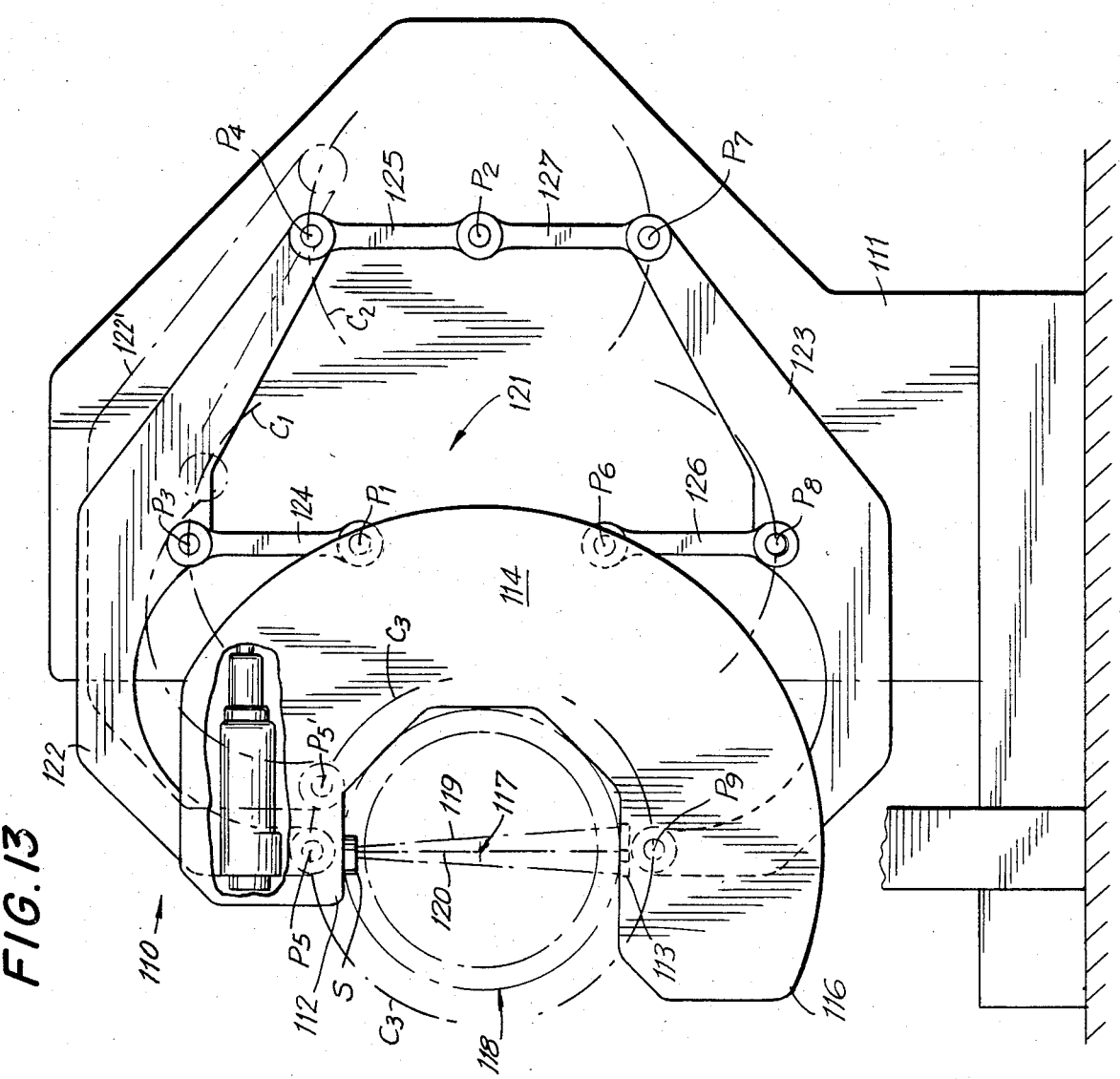
Figure 14:
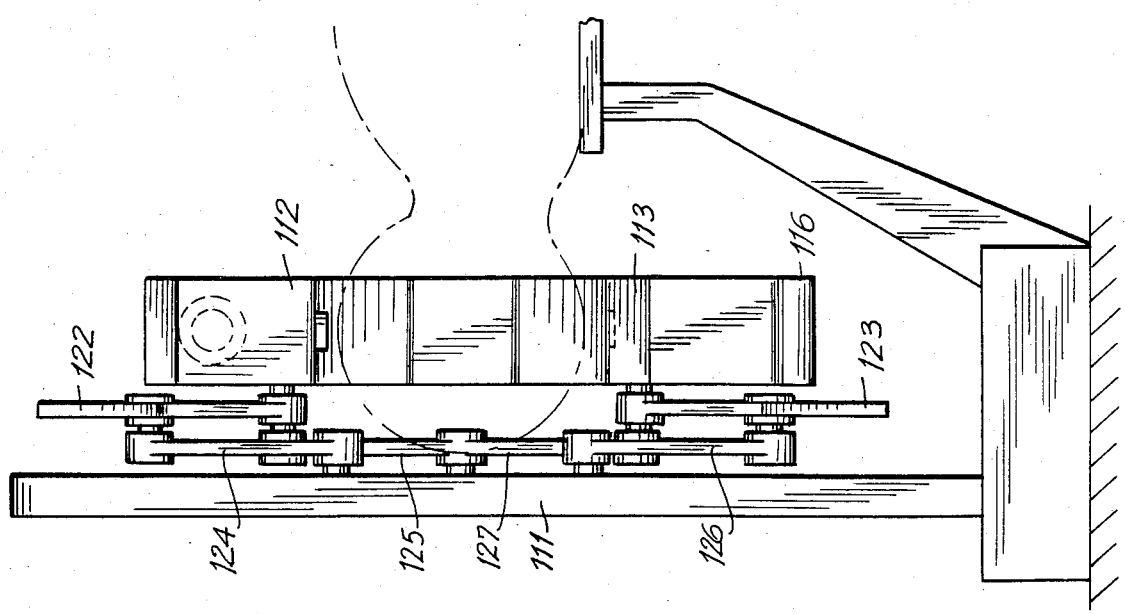
Figure 15:
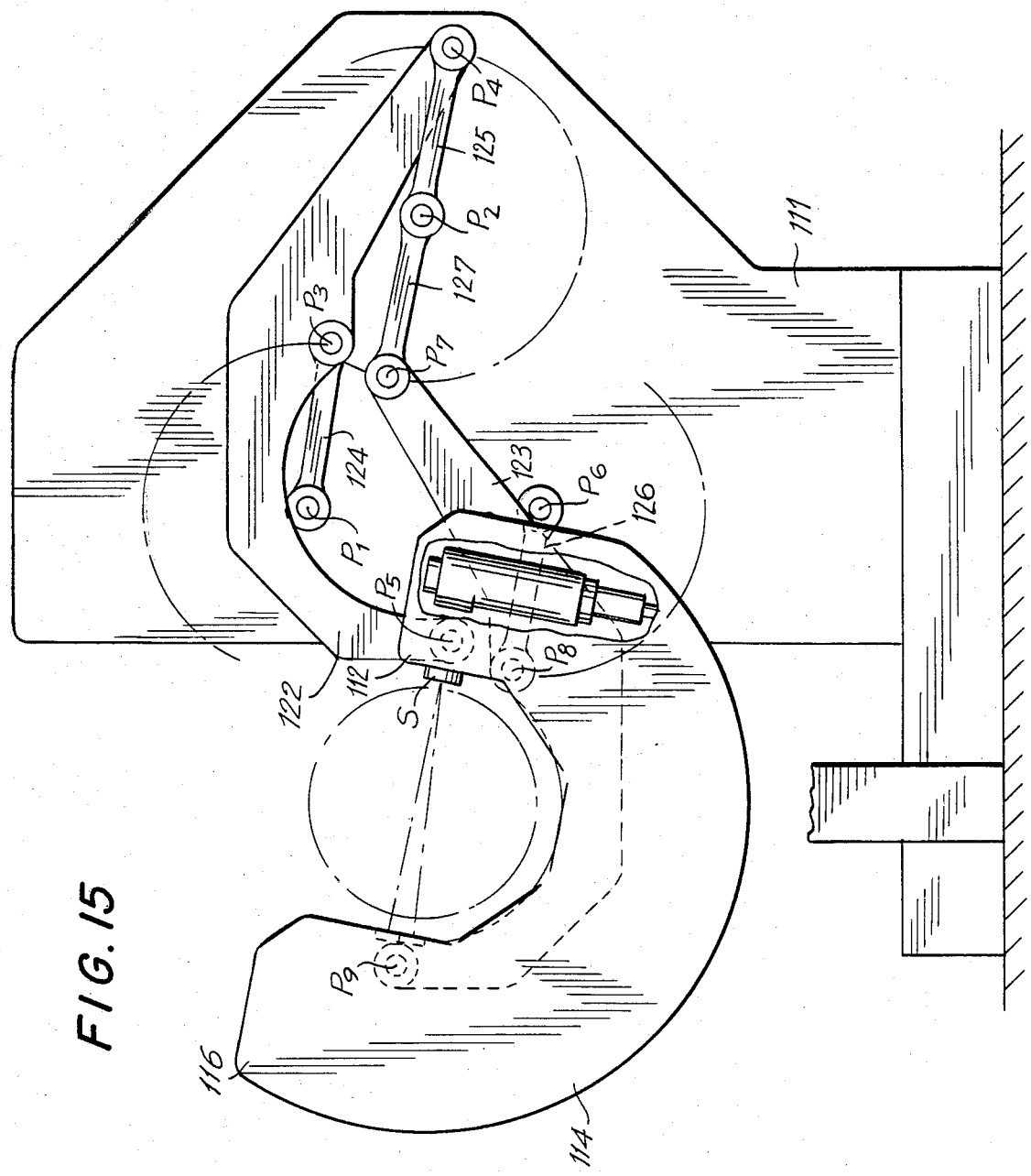
Figure 16A:
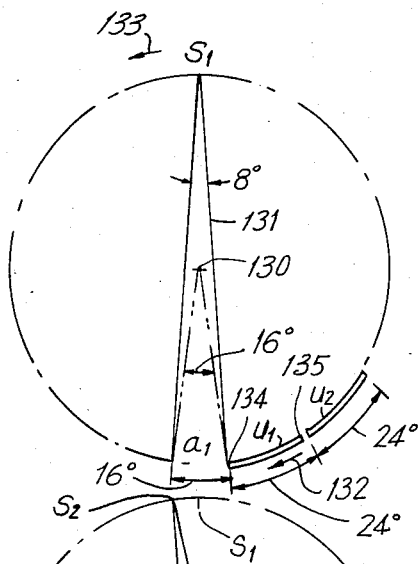
Figure 16B:
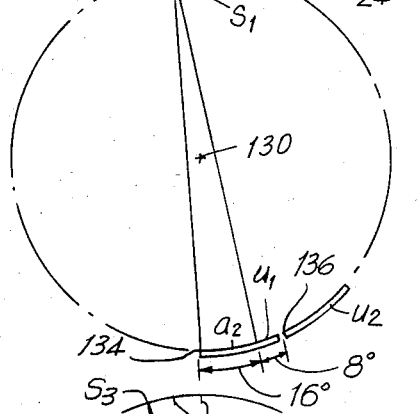
Figure 16C:
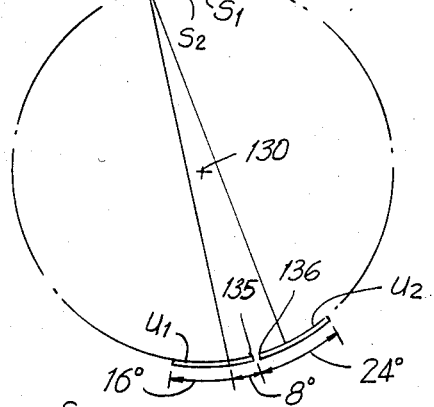
Figure 16D:
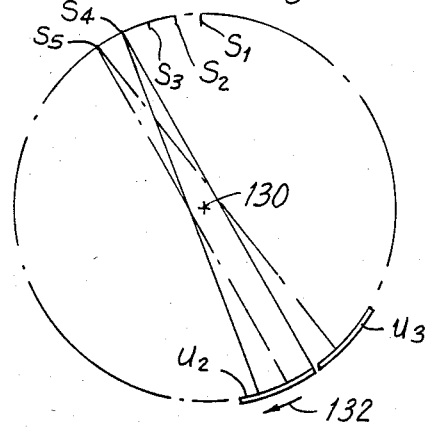
Figure 17:
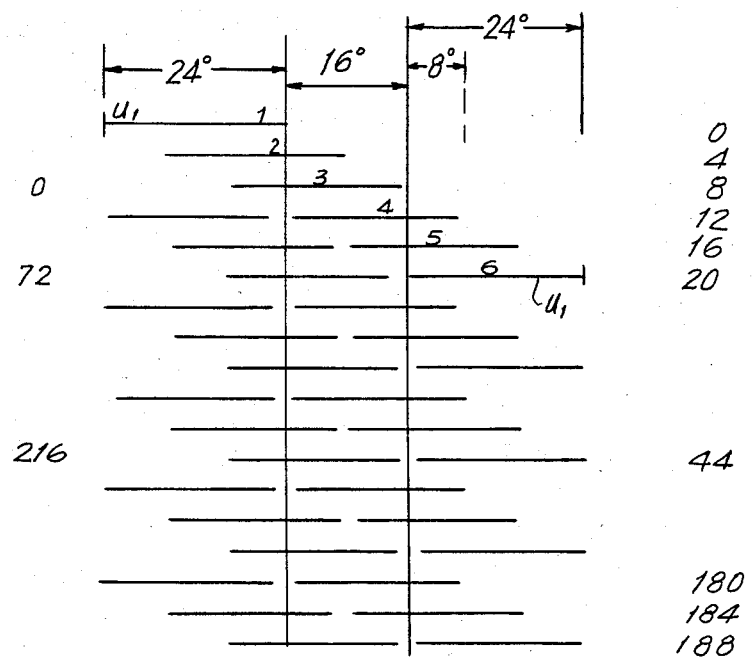
Figure 20:
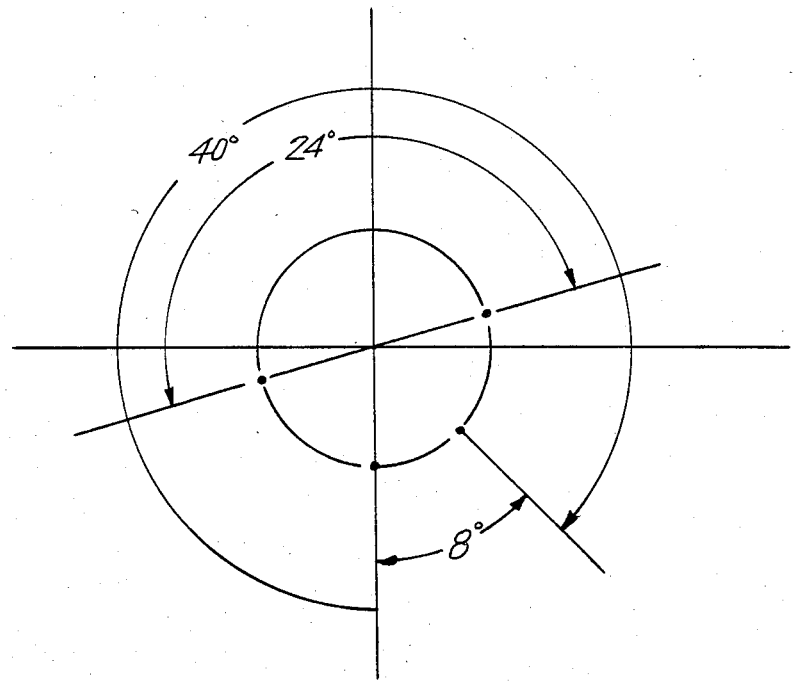
Figure 18:
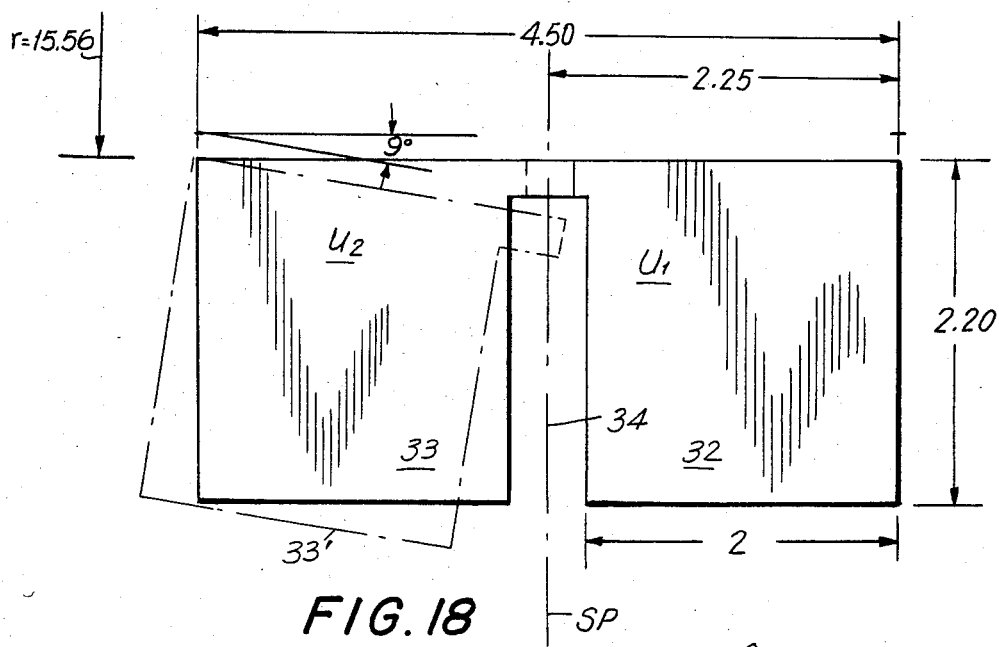
Figure 24:
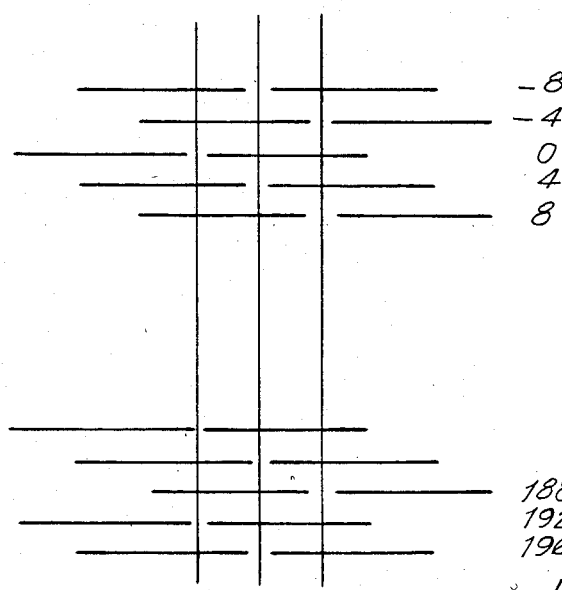
Figure 25:
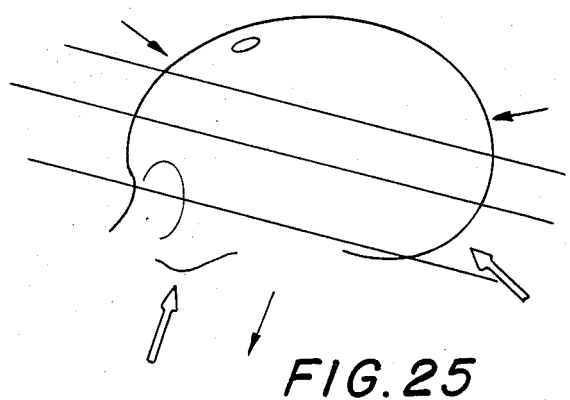
Figure 26:
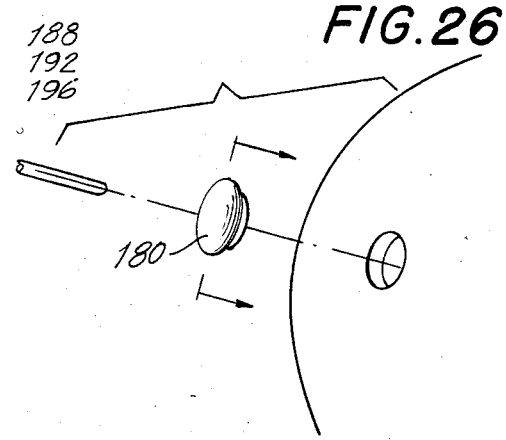

When using the above-described system it is obviously essential that the patient's skull be held immobile. A combination of three or more pins to engage the skull are preferably located at the two cheek bones and at the rear of the head above the neck, as generally illustrated in FIG. 13. This arrangement secures the patient's head while leaving most of the upper skull fully accessible for the boring of the access hole and the subsequent insertion of the probe. After the hole is drilled a rigid flanged guide ring 180 as generally shown in FIG. 14 may be used to positively establish the lateral coordinates of the axis of the aperture, and to establish a reference location in the axial direction for precise axial penetration of the probe, and to function as a temporary and partial seal.

The new system described herein not only provides far improved accessibility to the patient, but substantially reduces the radiation exposure time to the patient because of the almost continuous scanning motion in either angular direction without interruption. The scan period is approximately 30 seconds per plane in each direction, or one full minute per plane times 35 planes for a total of 35 minutes. A conventional apparatus would require one hour scan time. The analysis time is also substantially reduced, being essentially instant full volumetric versus conventional feedback via two projections. Finally it should be noted that conventional apparatuses are massive partially as a result of the full circular frame for supporting the radiation source and detector means and through which the patient is axially inserted and the associated structure for moving the patient. In the new invention the open C-shape frame is light and simple relative to the prior art and permits a far more simple patient support table.

The preferred embodiment described herein may be modified in numerous ways within the spirit and scope of the appended claims. Generally stated the invention is an improved positioning means for supporting and moving the source and detector means in a defined relationship relative to each other. A generally C-shaped frame securing the source and detector means in spaced-apart relationship with the radiation beam projected therebetween is rotated about a generally horizontal axis by first drive means comprising a precision electrical motor, whereby the source and detector are moved about a circumferential path and the rotated radiation beam defines a basic scanning plane. A second electrical motor drive means moves the frame carrying the source and detector axially for defining scan planes parallel to the basic plane; a third drive means carried by the frame in a first circumferential direction moves the detector means in the opposite circumferential direction while the radiation beam is projected onto the detector. To control and support the rotating frame, upper and lower arms are pivotally coupled to a base and to the frame to provide a pair of four-bar linkage parallelograms.

Since the preferred detector means comprises a pair of detector elements which are nominally coplanar and circumferentially adjacent, displacement means are provided for pivoting or otherwise displacing the lead detector element after its full forward excursion, out of alignment with the second detector and rearward to a new position behind the lead detector. More specific structural elements have been previously described herein; equivalent or substitute components are possible within the spirit and scope of the claims following.

We claim:

1. In a computerized tomographic scanning system including a base, a source or radiation, detector means comprising first and second detector units for receiving said radiation and producing scanning signals, and positioning means on said base for supporting and moving said source and detector means in a defined relationship relative to each other, the improvement in said positioning means comprising:

(a) a generally C-shaped frame having upper and lower arms, (b) means for securing said source to said upper arm and means for movably arranging said first and second detector units along a predetermined portion of said lower arm, said predetermined portion being disposed circumferentially opposite said source, (c) first drive means for rotating said frame about a nominally horizontal axis Z, thereby rotating said source and said predetermined portion of said lower arm in the same direction about a circumferential path, with the rotation of said beam defining a basic radiation scan plane, (d) second drive means for moving said frame along said Z axis for scanning in planes parallel to said basic plane and axially spaced along said Z axis, and (e) third drive means on said frame for moving said detector means circumferentially along said predetermined portion of said lower arm, particularly for moving said first and second detector units together, one leading the other, in a circumferential direction for a first predetermined distance relative to said predetermined portion and moving the leading one of said detector units in the opposite direction for a second predetermined distance relative to said predetermined portion after each movement of said detector units together for said first predetermined distance, while said radiation beam is projected between said source and said detector means such that at all times said beam impinges on at least one of said detector units.

2. A system according to claim 1 wherein (a) said radiation receiving surface has a generally circumferential length a, (b) said radiation beam projected by said source strikes an arc of length a' on said surface where a' < a, (c) said movement of said detector means circumferentially in a direction opposite that of said source causes said arc a and arc a' to move from an adjacent and non-overlying relationship into an overlying relationship, and then to an adjacent and non-overlying relationship.

3. A system according to claim 2, wherein said detector means has lead and trailing ends defining said arcuate length a, said lead end beginning said overlying relationship with said arc a' of the beam and said trailing end ending said relationship.

4. A system according to claim 3, wherein said first and second detector units are situated adjacent to each other, each having a lead end and a trailing end, said 3rd drive means positions the lead end of said second detector unit into overlying relationship with said arc a' of the beam as the trailing end of the first detector unit is concluding its overlying relationship with said arc a', said apparatus further comprising switch means for activating said detector units while they are in said overlying relationship.

5. Apparatus according to claim 2, wherein said beam defines an angle of approximately 8° and defines arc a' of approximately 16° on said detector means, and each of said detector units has arc length a equal to about 24°.

6. A system according to claim 2, wherein said first drive means moves said source and detector means continuously in one circumferential direction through an arc of at least 180° degrees, and subsequently moves said source and detector means in the opposite circumferential direction, said apparatus further comprising switch means for activating said detector means while it is moved in both directions.

7. Apparatus according to claim 3 wherein said positioning means further comprises a first arm having a near end, a far end pivotally attached to said upper arm of said frame, and an intermediate part, a first link of length r having one end pivotally secured to a first fixed point on said base and a second end pivotally coupled to the near end of said first arm, and a second link of length r having one end pivotally secured to a second fixed point on said base and a second end coupled to said intermediate part of said first arm, whereby said base, first and second links, and first arm comprise a parallelogram, four-bar linkage with said second ends of said first and second links and said tip end of said first arm all movable in identical circular arcuate paths of radius r, and wherein said first drive means comprises an electronic motor coupled to at least one component of said linkage for causing said tip end of said first arm carrying said source to traverse said circular path.

8. Apparatus according to claim 7 wherein said positioning means further comprises a second arm having a near end, a far end pivotally attached to said lower arm of said frame, and an intermediate part, third and fourth links similar to said first and second links for carrying and moving said source and said predetermined portion of said lower arm in a circular arc in the same circumferential direction in response to said first drive means.

9. Apparatus according to claim 8 wherein said first and third links are pivotally secured to the same fixed point on said base.

10. Apparatus according to claim 1 wherein said third drive means comprises a first part for moving each detector unit forward between initial and terminal positions, and a second part for moving each detector unit rearward back to its initial position while the other detector unit is moving forward and while said frame carrying said detector means is being moved circumferentially.

11. Apparatus according to claim 10 wherein said first part comprises an electric motor, an output drive element coupled to each of said detector units and a differential transmission coupled intermediate said motor and output drive element, and said second part comprises a Geneva mechanism coupled intermediate said motor differential transmission for temporarily reversing said output drive element.

12. Apparatus according to claim 11 wherein said first and second detector units when both are moving forward are situated so that their radiation receiving surfaces are aligned and generally coplanar, said third drive means further comprises displacement means coupled to each of said detector units for displacing each unit while it is being moved rearward, out of said alignment with said other detector unit, for preventing one unit from colliding with the other.

13. Apparatus according to claim 12 wherein said displacement means comprises means for pivoting each of said detector units, and cam-and-follower means intermediate and coupled to said detector units whereby each detector actuates said cam-and-follower means for pivoting the other detector.

14. Apparatus according to claim 5 wherein said radiation surface of each of said detector units comprises a plurality of detection elements, each of which has length in the circumferential direction corresponding to one third of one degree of arc, so that said 16° arc length a' defined by said beam overlies 48 of said detection elements at any moment in time of said scanning operation.

15. In a tomographic scanning system including a base, a source of penetrating energy, detector means comprising first and second detector units for receiving said energy and producing scanning signals, and positioning means on said base for supporting and moving said source and detector means in a defined relationship relative to each other, the improvement in said positioning means comprising:
 (a) a frame having first and second parts spaced apart from each other,
 (b) means for securing said source and detector means to said first and second part respectively for defining a radiation beam projected therebetween,
 (c) first drive means for rotating said frame about a first axis Z, thereby rotating said source and detector means about a circular path for rotating said radiation beam to define a basic radiation scan plane,
 (d) second drive means for moving said frame along said Z axis for establishing scan planes parallel to said basic plane and axially spaced along said Z axis, and
 (e) third drive means for repeatedly moving each of said first and second detector units along a predetermined portion of said second part of said frame in a circumferential direction alternately the same and opposite to the circumferential movement of said second part of said frame while said radiation beam is projected between said source and said detector units.

16. Apparatus according to claim 15 wherein said first and second detector units are situated adjacent to each other, one being nominally forward of the other, the two being movable together in a circumferential direction designated forward, said third drive means being coupled to said detector units for moving them together in said forward direction, then moving said forward unit rearward to the rear of the other while the other continues to move forward, and then moving both units forward together, this movement of detectors coinciding in time with said projection of said radiation beam between said source and said detector units, said units being adapted for receiving said radiation beam from said source at all times while moving forward.

17. In a computerized tomographic scanning system including a base, a source of radiation, detector means comprising first and second detector units for receiving said radiation and producing scanning signals, and positioning means on said base for supporting and moving said source and detector means in a defined relationship relative to each other, the improvement in said positioning means comprising:
 (a) a generally C-shaped frame having upper and lower arms,
 (b) means for securing said source to said upper arm and means for movably arranging said first and second detector units along a predetermined portion of said lower arm, said predetermined portion being disposed circumferentially opposite said source,
 (c) first drive means for rotating said frame about a nominally horizontal axis Z, thereby rotating said source and said predetermined portion of said lower arm in the same direction about a circumferential path, with the rotation of said beam defining a basic radiation scan plane, (d) second drive means for moving said frame along said Z axis for scanning in planes parallel to said basic plane and axially spaced along said Z axis, and (e) third drive means on said frame for moving said detector means circumferentially along said predetermined portion of said lower arm, particularly for moving said first and second detector units together, one leading the other, in a first circumferential direction for a first predetermined distance relative to said predetermined portion and moving the leading one of said detector units in a direction opposite said first direction for a second predetermined distance after each movement together for said first predetermined distance, while said radiation beam is projected between said source and said detector means such that at all times said beam impinges on at least one of said detector units.

* * * * *

UNITED STATES PATENT AND TRADEMARK OFFICE
CERTIFICATE OF CORRECTION

PATENT NO. : 4,501,009
DATED : February 19,1985
INVENTOR(S) : Manlio Abele

Page 1 of 2

It is certified that error appears in the above-identified patent and that said Letters Patent are hereby corrected as shown below:

Figures 1-12 should be deleted and Figures 13-26 should be renumbered as Figures 1-14.

In col. 6, line 3, change "23" to --11--;
line 49, delete "and corresponding rotation of";
line 50, delete "frame 114";
line 64, delete the comma after "al";
line 66, change "al, reprresents" to --al represents--.
In col. 8, line 39, change "annular" to --angular--.
In col. 11, line 4, change "whereever" to --wherever--;
line 28, delete "the" (second occurrence);
line 29, change "until" to --unit--;
line 62, change "follow" to --follower--;
line 63, change "pint" to --pin--.

In col. 13, line 63, change "or" to --of--.
In col. 14, line 36, insert --of each of said detector units-- after "surface";
line 39, change "means" to --units--;
line 40, change "in a direction opposite that of said source" to --for said first predetermined distance--;
line 41, insert --of said trailing detector unit-- before "and";
line 42, change "into" to --to--;
line 45, insert --each of-- before "said";

UNITED STATES PATENT AND TRADEMARK OFFICE
CERTIFICATE OF CORRECTION

PATENT NO. : 4,501,009
DATED : February 19, 1985
INVENTOR(S) : Manlio Abele

It is certified that error appears in the above-identified patent and that said Letters Patent is hereby corrected as shown below:

Col. 14, line 46, change "means" to --units-- and "lead" to --leading--;
line 47, change "lead" to --leading--;
line 52, change "lead" to --leading-- and "3rd" to --third--;
line 53, change "lead" to --leading--;
line 55, change "as" to --immediately after--, change "the" (third occurrence) to --said--, and delete "is;
line 56, change "concluding its" to --has entered into--;
line 58, change "they" to --portions thereof--;
line 59, change "relationship." to --relationship such that there is no interruption in detection.--.

Signed and Sealed this

Twenty-ninth Day of October 1985

[SEAL]

Attest:

Attesting Officer

DONALD J. QUIGG

Commissioner of Patents and Trademarks—Designate